US009399029B2

(12) United States Patent
Tanaka et al.

(10) Patent No.: US 9,399,029 B2
(45) Date of Patent: Jul. 26, 2016

(54) IMMUNE TOLERANCE INDUCER

(71) Applicants: SBI PHARMACEUTICALS CO., LTD., Minato-ku, Tokyo (JP); National Center for Child Health and Development, Setagaya-ku, Tokyo (JP)

(72) Inventors: Tohru Tanaka, Tokyo (JP); Motowo Nakajima, Tokyo (JP); Fuminori Abe, Tokyo (JP); Naomi Haga, Tokyo (JP); Kiwamu Takahashi, Tokyo (JP); Hidenori Ito, Tokyo (JP); Ko Rii, Tokyo (JP)

(73) Assignees: SBI Pharmaceuticals Co., Ltd., Tokyo (JP); National Center for Child Health and Development, Tokyo (JP)

( * ) Notice: Subject to any disclaimer, the term of this patent is extended or adjusted under 35 U.S.C. 154(b) by 0 days.

(21) Appl. No.: 14/413,151

(22) PCT Filed: Jul. 3, 2013

(86) PCT No.: PCT/JP2013/004130
§ 371 (c)(1),
(2) Date: Jan. 6, 2015

(87) PCT Pub. No.: WO2014/010206
PCT Pub. Date: Jan. 16, 2014

(65) Prior Publication Data
US 2015/0174090 A1    Jun. 25, 2015

(30) Foreign Application Priority Data

Jul. 13, 2012  (JP) ................................ 2012-157374

(51) Int. Cl.
A61K 31/197    (2006.01)
A61K 33/26    (2006.01)
(Continued)

(52) U.S. Cl.
CPC ............. *A61K 31/197* (2013.01); *A61K 31/194* (2013.01); *A61K 33/26* (2013.01);
(Continued)

(58) Field of Classification Search
None
See application file for complete search history.

(56) References Cited

U.S. PATENT DOCUMENTS 5,756,492 A    5/1998    Buelow et al.
8,563,605 B2   10/2013   Miyanari et al.
(Continued)

FOREIGN PATENT DOCUMENTS

EP    1785132 A1    5/2007
JP    2000-191401 A    7/2000
(Continued)

OTHER PUBLICATIONS

Scleroderma: MedlinePlus Medical Encyclopedia available at <<www.nlm.nih.gov/medlineplus/ency/article/000429.htm>> visited Nov. 2, 2015.*

(Continued)

*Primary Examiner* — Karl J Puttlitz
(74) *Attorney, Agent, or Firm* — Foley & Lardner LLP

(57) ABSTRACT

An object of the present invention is to provide a regulatory dendritic cell inducing agent applicable to the treatment of immune disease as well as an immune tolerance inducing agent such as a preventive and/or therapeutic agent for allergic disease and a preventive and/or therapeutic agent for autoimmune disease, both of which are safe and have the mechanism of action different from that of conventional drugs. As a means for achieving the above object, an immune tolerance inducing agent comprising 5-aminolevulinic acid (ALA) or a derivative thereof, or a salt of the 5-ALA or the derivative and an iron compound as active ingredients is prepared. Preferable examples of the ALAs can include ALA and various esters such as methyl ester, ethyl ester, propyl ester, butyl ester, and pentyl ester of ALA, and their hydrochlorides, phosphates, and sulfates. Preferable examples of the iron compound can include sodium ferrous citrate.

20 Claims, 15 Drawing Sheets

(51) Int. Cl.
| | |
|---|---|
| *C12N 5/0784* | (2010.01) |
| *A61K 38/19* | (2006.01) |
| *A61K 31/194* | (2006.01) |
| *A61K 38/40* | (2006.01) |

(52) U.S. Cl.
CPC .............. *A61K 38/193* (2013.01); *A61K 38/40* (2013.01); *C12N 5/064* (2013.01); *C12N 2500/24* (2013.01); *C12N 2501/052* (2013.01); *C12N 2501/22* (2013.01); *C12N 2501/2304* (2013.01)

(56) References Cited

U.S. PATENT DOCUMENTS

| | | | |
|---|---|---|---|
| 2004/0171601 | A1 | 9/2004 | Fukumura et al. |
| 2004/0235162 | A1 | 11/2004 | Sato |
| 2005/0032210 | A1 | 2/2005 | Sato et al. |
| 2009/0130227 | A1* | 5/2009 | Ito ........................... A61K 8/44 424/646 |
| 2010/0061965 | A1 | 3/2010 | Connolly et al. |
| 2011/0196033 | A1 | 8/2011 | Tanaka |
| 2012/0213808 | A1 | 8/2012 | Murakami et al. |
| 2013/0052734 | A1 | 2/2013 | Todo et al. |
| 2013/0108710 | A1 | 5/2013 | Tanaka et al. |
| 2014/0188034 | A1 | 7/2014 | Tanaka et al. |
| 2014/0249217 | A1 | 9/2014 | Rii et al. |

FOREIGN PATENT DOCUMENTS

| | | | |
|---|---|---|---|
| JP | 2000-344602 | A | 12/2000 |
| JP | 2011016753 | * | 1/2001 |
| JP | 2002-060301 | A | 2/2002 |
| JP | 2003-530101 | A | 10/2003 |
| JP | 2004-298181 | A | 10/2004 |
| JP | 2004-300098 | A | 10/2004 |
| JP | 2005-508864 | A | 4/2005 |
| JP | 2005-306749 | A | 11/2005 |
| JP | 2006-069963 | A | 3/2006 |
| JP | 2006-096745 | A | 4/2006 |
| JP | 2006-290761 | A | 10/2006 |
| JP | 2006-316000 | A | 11/2006 |
| JP | 2007-131598 | A | 5/2007 |
| JP | 2008-115089 | A | 5/2008 |
| JP | 2009-143939 | A | 7/2009 |
| JP | 2009-221128 | A | 10/2009 |
| JP | 2009-298739 | A | 12/2009 |
| JP | 4547174 | B2 | 7/2010 |
| JP | 2011-016753 | A | 1/2011 |
| JP | 2011-505378 | | 2/2011 |
| JP | 2011-522837 | A | 8/2011 |
| WO | WO 95/02323 | | 1/1995 |
| WO | WO 01/77299 | A2 | 10/2001 |
| WO | WO 02/098431 | A1 | 12/2002 |
| WO | WO 2009/073599 | A1 | 6/2009 |
| WO | WO 2009/139156 | | 11/2009 |
| WO | WO 2009/149397 | | 12/2009 |
| WO | WO 2010/050179 | A1 | 5/2010 |
| WO | WO 2011/048766 | A1 | 4/2011 |
| WO | WO 2011/105394 | A1 | 9/2011 |
| WO | WO 2011/145343 | A1 | 11/2011 |
| WO | WO 2012/172821 | A1 | 12/2012 |
| WO | WO 2013/054470 | | 4/2013 |

OTHER PUBLICATIONS

Egli et al., "Sensitivity of osteoblasts, fibroblasts, bone marrow cells, and dendritic cells to 5-aminolevulinic acid based photodynamic therapy," Journal of Photochemistry and Photobiology B: Biology, Nov. 2007, 89(2-3)70-77.

Hryhorenko et al., "Deletion of Alloantigen-Activated Cells by Aminolevulinic Acid-Based Photodynamic Therapy," Photochemistry and Photobiology, Jan. 1, 1999, 69(5):560-565.

Cai et al., "Carbon monoxide generated by 5-aminolevulinic acid results in cardiac allograft permanent acceptance by increasing regulatory T cell generation," Proceedings of the Japanese Society for Immunology, Nov. 2012, 41:55, 1-F-W10-7-O/P.

Evangelou et al., "Topical aminolaevulinic acid-photodynamic therapy produces an inflammatory infiltrate but reduces Langerhans cells in healthy human skin *in vivo*," British Journal of Dermatology, 2011, 165(3):513-519.

Hayami et al., "Immunosuppression by Photodynamic therapy," 27th Japanese Society for Photomedicine and Photobiology, Aug. 6-7, 2007, p. 61, with English translation.

Hayami et al., "Immunosuppressive effects of photodynamic therapy by topical aminolevulinic acid," Journal of Dermatology, 2007, 34(5):320-327.

Hryhorenko et al., "Antigen specific and nonspecific modulation of the immune response by aminolevulinic acid based photodynamic therapy," Immunopharmacology, 1998, 40(3):231-240.

Iwata, Makoto, "Role of retinoic acid in gut immunity," Chemistry and Biology, 2010 48(6):389-394, with partial English translation.

Matsushima et al., "Protective Effect of Coenzyme Q10 on Canine Myocardial Injury Caused by Ischemia and Reperfusion," Japanese Journal of Transplantation, 1990, 25(3):279-282, with English summary on first page.

Ran at al., "ALA-PDT alleviates graft-versus-host disease in mice following allogenic bone marrow transplantation," Chinese Journal of Contemporary Pediatrics, 2006, 8(5):408-412, with English abstract on first page.

Ran et al., "Effects of 5-aminolevulinic acid-mediated photodynamic therapy on GVHD and GVL following Allo-BMT in ALL mice," Journal of Clinical Pediatrics, 2007, 25(8):655-659.

Bhattacharya et al., "GM-CSF-induced bone-marrow-derived dendritic cells can expand natural Tregs and induce adaptive Tregs by different mechanisms," Journal of Leukocyte Biology, Feb. 2011, 89:235-249.

Database WPI Week 201247 Thomson Scientific, London, GB; AN 2012-H52091, XP002752960, & JP 2012 121918 A (Cosmo Oil Co. Ltd.) Jun. 28, 2012, abstract.

Kitajima et al., "5-Aminolevulinic acid induces permanent acceptance of murine cardiac allografts via induction of regulator dendritic cells and expansion of alloantigen-specific Tregs. (P2176)," The Journal of Immunology, May 1, 2013, 190:69.26, P2176, XP009187997, abstract.

Corthay, A., "How do Regulatory T Cells Work?", Journal of Immunology, 2009, 70(4):326-336.

Oellinger et al., "Role of heme oxygenase-1 in transplantation," Transplant International, 2010, 23(11):1071-1081.

Rocuts et al., "Bilirubin Promotes De Novo Generation of T Regulatory Cells," Cell Transplantation, 2010, 19(4):443-451.

Wachowska et al., "Aminolevulinic Acid (ALA) as a Prodrug in Photodynamic Therapy of Cancer," Molecules, May 19, 2011, 16:4140-4164.

* cited by examiner

ALA-treated DC significantly suppress alloreactive T cell proliferation

ALA-treated DC significantly increase the generation of Foxp3+ Treg cells

The potential of the ALA-treated DC induce alloreactive T cell proliferation

ALA-treated DC increase the generation of Foxp3+ Treg cells

Control, No ALA and ALA-treated

IMMUNE TOLERANCE INDUCER

CROSS-REFERENCE TO RELATED APPLICATIONS

This application is a National Stage application of PCT/JP2013/004130, filed Jul. 3, 2013, which claims priority from Japanese application JP 2012-157374, filed Jul. 13, 2012.

TECHNICAL FIELD

The present invention relates to an immune tolerance inducing agent, more particularly, to an immune tolerance inducing agent comprising 5-aminolevulinic acid (ALA) or a derivative thereof, or a salt of the 5-ALA or the derivative, which is applied to induction of regulatory dendritic cells, and also to allergic disease, autoimmune disease, and the like. The immune tolerance inducing agent of the present invention is useful for the induction of regulatory dendritic cells, and also for the treatment or prevention of diseases caused by unnecessary immune reactions such as allergic disease and autoimmune disease.

BACKGROUND ART

Immune tolerance refers to a state in which the immune system does not attack a substance that could be an antigen. Immune tolerance can occur in the form of "self-tolerance," meaning that the immune response is not generally mounted against self-antigens, or "acquired tolerance," which is induced even against non-self-antigens under certain administration conditions. With regard to non-self-antigens, active suppression by regulatory T cells is assumed to be involved. Diseases in which immune tolerance is required such as allergic disease and autoimmune disease can be perceived as phenomena in which immunological unresponsiveness to self or non-self is collapsed.

Dendritic cells are lineage marker-negative, MHC class II-positive antigen presenting cells having dendrites. Hematopoietic stem cells are differentiated into immature dendritic cells, and further into mature dendritic cells via the myeloid and lymphoid pathways. Dendritic cells are widely present in the peripheral non-lymphatic tissues and lymphatic tissues in a variety of subsets of different differentiation lineages and levels of maturity. In the steady state (non-inflammatory state), the majority of dendritic cells remain immature, and upon weak antigenic stimulation and antigen presentation that may provide costimulation, immature dendritic cells induce clonal deletion and inactivation of naive T cells, while inducing and amplifying various regulatory T cells having immunosuppressive capacity. In light of this, immature dendritic cells are assumed to play an important role in the maintenance of immunological homeostasis via induction of immune tolerance associated with these regulatory mechanisms controlling T cell function. Meanwhile, in an inflammatory state caused by the invasion of exogenous antigens such as bacteria, viruses, and foreign bodies, immature dendritic cells that have ingested these exogenous antigens are differentiated into mature dendritic cells by inflammatory stimulation. As the most potent antigen presenting cells, mature dendritic cells provide antigenic stimulation and costimulation to naive T cells to induce them to differentiate into antigen-specific effector T cells, thereby inducing immune response. Also, as antigen presenting cells exhibiting potent immune tolerance-inducing capacity even in an inflammatory state, regulatory dendritic cells (also referred to as tolerogenic dendritic cells in some cases) are known.

In regard to regulatory dendritic cells, a method for inducing human immunoregulatory dendritic cells by culturing human dendritic cells or precursor cells thereof with cytokines including at least IL-10 and TGF-β in vitro, human immunoregulatory dendritic cells obtained by the above method, and a pharmaceutical composition comprising the above human immunoregulatory dendritic cells (see Patent Document 1), a method of producing tolerogenic dendritic cells, including the step of incubating isolated dendritic cells with respiratory syncytial virus in an amount sufficient to infect the dendritic cells under conditions that trigger the cell surface expression of the following cell surface $CD80^{high}$, $CD86^{high}$, $CD40^{high}$ and $CD83^{low}$ (see Patent Document 2), and technology relevant to a preventive or therapeutic agent for diseases induced by excessive secretion of inflammatory cytokines (for example, sepsis), an IL-10 production promoting agent, an apoptosis inhibitory agent, and the like, all of which comprise regulatory dendritic cells (see Patent Document 3), are known.

ALA is known as an intermediate in tetrapyrrole biosynthesis pathways present in a wide range of animals, plants, or bacteria. This acid is commonly biosynthesized from succinyl CoA and glycine by 5-aminolevulinic acid synthase. Photodynamic therapy using ALA (hereinafter, also referred to as "ALA-PDT") has also been developed and has received attention as a low invasive treatment method capable of maintaining QOL. For example, diagnostic or therapeutic agents for tumor comprising ALA and so on have been reported. In addition, ALA is also known to be useful as a preventing and improving agent or a therapeutic agent for adult disease, cancer, or male sterility (see e.g., Patent Documents 4 to 6).

PRIOR ART DOCUMENTS

Patent Documents

Patent Document 1: Japanese unexamined Patent Application Publication No. 2004-298181

Patent Document 2: Japanese unexamined Patent Application Publication (Translation of PCT Application) No. 2011-522837

Patent Document 3: Japanese unexamined Patent Application Publication No. 2006-290761

Patent Document 4: International Publication No. WO2010/050179

Patent Document 5: Japanese unexamined Patent Application Publication No. 2011-16753

Patent Document 6: International Publication No. WO2009/139156

SUMMARY OF THE INVENTION

Object to be Solved by the Invention

An object of the present invention is to provide a regulatory dendritic cell inducing agent applicable to the treatment of immune disease as well as an immune tolerance inducing agent such as a preventive and/or therapeutic agent for allergic disease and a preventive and/or therapeutic agent for autoimmune disease, both of which are safe and have the mechanism of action different from that of conventional drugs.

Means to Solve the Object

The present inventors have continued various studies on the medical application of ALA and found that ALA alone or a composition comprising ALAs and an iron compound such as sodium ferrous citrate (SFC), which is an iron ion donor, has regulatory dendritic cell inducing effect, allergic disease preventing and/or treating effect, and autoimmune disease preventing and/or treating effect.

In addition, the present inventors found that an iron compound collaborates with ALA to potentiate the regulatory dendritic cell inducing effect, allergic disease preventing and/or treating effect, and autoimmune disease preventing and/or treating effect. The administration of ALA alone may suffice in the presence of the abundant iron compound or in the case where the iron compound is separately taken. Among minerals, iron is often lacking in Japanese, who take a smaller amount of lean meat than foreign people. For this reason, ALA was added together with the iron compound in some Examples directed to Japanese. This is not necessary in the case where the subject is a person with sufficient iron storage. Also, ALA is widely known to be metabolized into porphyrin, which exhibits PDT or PDD activity upon light irradiation. The method for inducing regulatory dendritic cells, the method for preventing and/or treating allergic disease, and the method for preventing and/or treating autoimmune disease according to the present invention do not require light.

The present inventors have further conducted diligent studies on administration methods and doses and consequently established an immune tolerance inducing agent, comprising ALAs alone, or ALAs and an iron compound as active ingredients. Based on these findings, the present invention has been completed.

Specifically, the present invention is as follows.

[1] An immune tolerance inducing agent, containing a compound represented by the following formula (I) or a salt thereof:

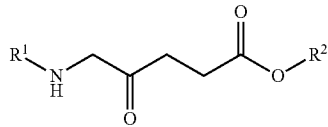

(wherein $R^1$ represents a hydrogen atom or an acyl group; and $R^2$ represents a hydrogen atom, a linear or branched alkyl group, a cycloalkyl group, an aryl group, or an aralkyl group).

[2] The immune tolerance inducing agent according to [1], wherein $R^1$ and $R^2$ each represent a hydrogen atom.

[3] The immune tolerance inducing agent according to [1] or [2], further containing an iron compound.

[4] The immune tolerance inducing agent according to [3], wherein the iron compound is one or more compound(s) selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylene diaminetetraacetate, iron ammonium ethylene diaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

[5] The immune tolerance inducing agent according to [3], wherein the iron compound is sodium ferrous citrate.

[6] The immune tolerance inducing agent according to any one of [1] to [5], wherein the agent is applied to induction of a regulatory dendritic cell.

[7] The immune tolerance inducing agent according to any one of [1] to [5], wherein the agent is applied to an allergic disease.

[8] The immune tolerance inducing agent according to [7], wherein the allergic disease is atopic dermatitis.

[9] The immune tolerance inducing agent according to any one of [1] to [5], wherein the agent is applied to an autoimmune disease.

[10] The immune tolerance inducing agent according to [9], wherein the autoimmune disease is scleroderma.

[11] A method for inducing immune tolerance, comprising administering the immune tolerance inducing agent according to any one of [1] to [10] to a subject.

[12] A method for inducing a regulatory dendritic cell, comprising administering the immune tolerance inducing agent according to any one of [1] to [5] to a subject.

[13] A method for inducing a regulatory dendritic cell, comprising treating in vitro a cell obtained from a bone marrow with the immune tolerance inducing agent according to any one of [1] to [5] and GM-CSF.

[14] An isolated regulatory dendritic cell induced by the method according to [12] or [13].

[15] A method for preventing and/or treating an allergic disease, comprising administering the immune tolerance inducing agent according to any one of [1] to [5] to a subject.

[16] A method for preventing and/or treating an autoimmune disease, comprising administering the immune tolerance inducing agent according to any one of [1] to [5] to a subject.

[17] A kit for inducing immune tolerance, comprising a) a compound represented by the following formula (I) or a salt thereof:

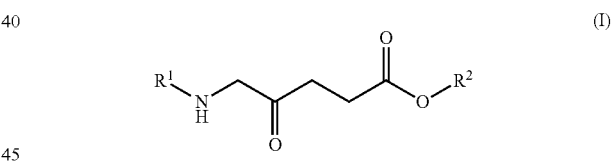

(wherein $R^1$ represents a hydrogen atom or an acyl group; and $R^2$ represents a hydrogen atom, a linear or branched alkyl group, a cycloalkyl group, an aryl group, or an aralkyl group); and
b) an iron compound.

[18] A method for inducing immune tolerance, comprising administering a) a compound represented by the following formula (I) or a salt thereof:

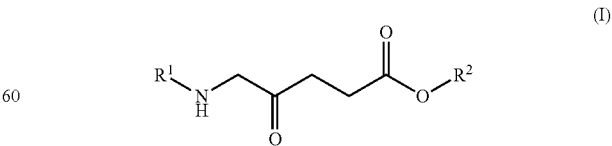

(wherein $R^1$ represents a hydrogen atom or an acyl group; and $R^2$ represents a hydrogen atom, a linear or branched alkyl group, a cycloalkyl group, an aryl group, or an aralkyl group); and b) an iron compound,
simultaneously or one after another to a subject.

[19] A kit for inducing a regulatory dendritic cell in vitro, comprising
a) the immune tolerance inducing agent according to any one of [1] to [5]; and
b) GM-CSF.

[20] A combination of preventive and/or therapeutic agents for an allergic disease, comprising
a) the immune tolerance inducing agent according to any one of [1] to [5]; and
b) a therapeutic drug for allergic disease.

[21] A combination of preventive and/or therapeutic agents for allergic disease, comprising
a) a compound represented by the following formula (I) or a salt thereof:

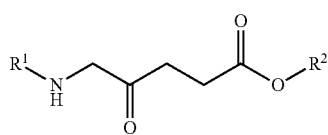

(wherein $R^1$ represents a hydrogen atom or an acyl group; and $R^2$ represents a hydrogen atom, a linear or branched alkyl group, a cycloalkyl group, an aryl group, or an aralkyl group);
b) an iron compound; and
c) a therapeutic drug for allergic disease.

[22] A combination of preventive and/or therapeutic agents for autoimmune disease, comprising
a) an immune tolerance inducing agent according to any one of [1] to [5]; and
b) a therapeutic drug for autoimmune disease.

[23] A combination of preventive and/or therapeutic agents for autoimmune disease, comprising
a) a compound represented by the following formula (I) or a salt thereof:

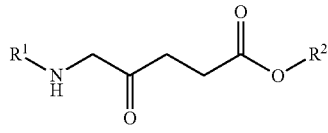

(wherein $R^1$ represents a hydrogen atom or an acyl group; and $R^2$ represents a hydrogen atom, a linear or branched alkyl group, a cycloalkyl group, an aryl group, or an aralkyl group);
b) an iron compound; and
c) a therapeutic drug for autoimmune disease.

Examples of other aspects of these inventions can include the following.

[24] A regulatory dendritic cell inducing agent, comprising a compound represented by the formula (I) or a salt thereof.
[25] The regulatory dendritic cell inducing agent according to [24], further comprising an iron compound.
[26] A method for inducing a regulatory dendritic cell, comprising administering the regulatory dendritic cell inducing agent according to [24] or [25] to a subject.
[27] A compound represented by the formula (I) or a salt thereof to be used for the induction of a regulatory dendritic cell.
[28] A composition comprising a compound represented by the formula (I) or a salt thereof and an iron compound to be used for the induction of a regulatory dendritic cell.
[29] Use of a compound represented by the formula (I) or a salt thereof for the preparation of a regulatory dendritic cell-inducing agent.
[30] Use of a compound represented by the formula (I) or a salt thereof and an iron compound for the preparation of a regulatory dendritic cell-inducing agent.
[31] A preventive and/or therapeutic agent for allergic disease, comprising a compound represented by the formula (I) or a salt thereof.
[32] The preventive and/or therapeutic agent for allergic disease according to [31], further comprising an iron compound.
[33] A method for preventing and/or treating allergic disease, comprising administering the preventive and/or therapeutic agent for allergic disease according to [31] or [32] to a subject.
[34] A compound represented by the formula (I) or a salt thereof to be used for the prevention and/or treatment of allergic disease.
[35] A composition comprising a compound represented by the formula (I) or a salt thereof and an iron compound, to be used for the prevention and/or treatment of allergic disease.
[36] Use of a compound represented by the formula (I) or a salt thereof for the preparation of a preventive and/or therapeutic agent for allergic disease.
[37] Use of a compound represented by the formula (I) or a salt thereof and an iron compound for the preparation of a preventive and/or therapeutic agent for allergic disease.
[38] A preventive and/or therapeutic agent for autoimmune disease, comprising a compound represented by the formula (I) or a salt thereof.
[39] The preventive and/or therapeutic agent for autoimmune disease according to [38], further comprising an iron compound.
[40] A method for preventing and/or treating autoimmune disease, comprising administering the preventive and/or therapeutic agent for autoimmune disease according to [38] or [39] to a subject.
[41] A compound represented by the formula (I) or a salt thereof to be used for the prevention and/or treatment of autoimmune disease.
[42] A composition comprising a compound represented by the formula (I) or a salt thereof and an iron compound, to be used for the prevention and/or treatment of autoimmune disease.
[43] Use of a compound represented by the formula (I) or a salt thereof for the preparation of a preventive and/or therapeutic agent for autoimmune disease.
[44] Use of a compound represented by the formula (I) or a salt thereof and an iron compound for the preparation of a preventive and/or therapeutic agent for autoimmune disease.

Effect of the Invention

The immune tolerance inducing agent of the present invention can induce regulatory dendritic cells, which are applicable to the treatment of immune diseases. Also, the immune tolerance inducing agent of the present invention can prevent and/or treat allergic disease and prevent and/or treat autoimmune disease. The immune tolerance inducing agent of the present invention differs in the mechanism of action from conventional immunosuppressants or the like and is thus expected to enhance effects by combined use with existing drugs.

MODE OF CARRYING OUT THE INVENTION

Figure 1:
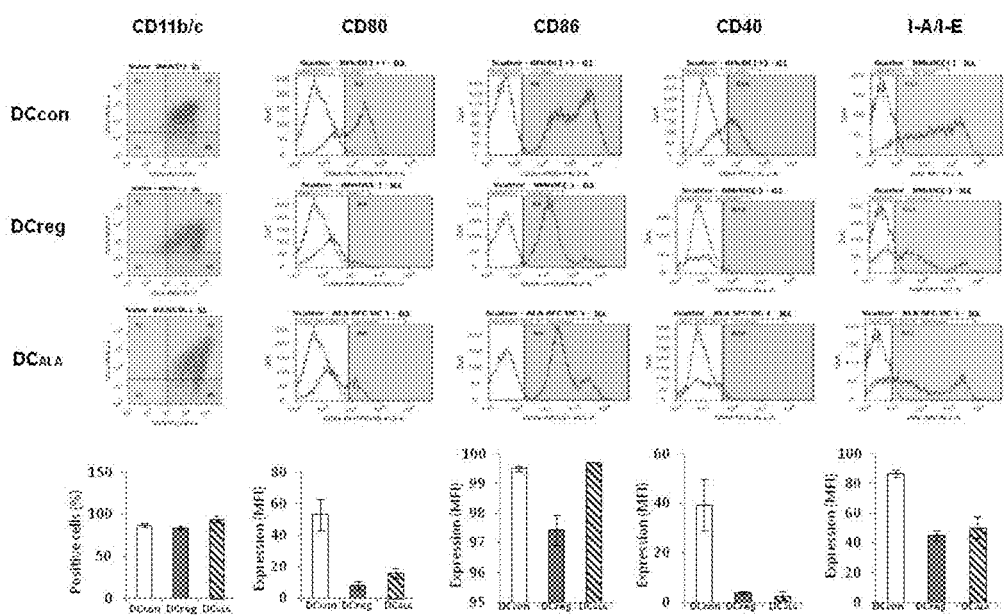
FIG. 1 is a set of diagrams showing the results of the expression of the dendritic cell-specific surface markers.

In the present invention, the phrase "induction of immune tolerance" refers to induction of a state in which the immune reaction against a specific antigen induced by ALAs or ALAs and an iron compound is suppressed, in other words, induction of a reduced immune reaction level, a retardation in the development or progression of immune reaction, and/or a reduced risk of immune reaction. The immune tolerance inducing agent of the present invention is not particularly limited as long as the agent comprises a compound represented by the formula (I) or a salt thereof (hereinafter, they are also collectively referred to as "ALAs") as an active ingredient. For the immune tolerance inducing agent of the present invention, it is preferred to contain an iron compound in addition to ALAs. The immune tolerance inducing agent of the present invention, particularly, the immune tolerance inducing agent, containing ALAs and an iron compound, can be administered to a subject including humans as well as livestock/fowl or pets to thereby induce immune tolerance or regulatory dendritic cells, and moreover, enable prevention and/or treatment of allergic disease and prevention and/or treatment of autoimmune disease. It should be noted that when the immune tolerance inducing agent and the kit for inducing immune tolerance according to the present invention are applied to induction of regulatory dendritic cells, they may be referred to as a "regulatory dendritic cell inducing agent" and a "kit for inducing a regulatory dendritic cell in vitro," respectively, and when the immune tolerance inducing agent and the kit for inducing immune tolerance according to the present invention are applied to allergic disease, they may be referred to as a "preventive and/or therapeutic agent for allergic disease" and a "preventive and/or therapeutic kit for allergic disease," respectively, and when the immune tolerance inducing agent and the kit for inducing immune tolerance according to the present invention are applied to autoimmune disease, they may be referred to as a "preventive and/or therapeutic agent for autoimmune disease" and a "preventive and/or therapeutic kit for autoimmune disease," respectively.

The kit for inducing immune tolerance of the present invention is not particularly limited as long as the kit comprises ALAs and an iron compound (as individual drugs) as active ingredients and is used for inducing immune tolerance. Use of the kit for inducing immune tolerance enables induction of immune tolerance and regulatory dendritic cells, prevention and/or treatment of allergic disease, and prevention and/or treatment of autoimmune disease in a subject including humans as well as livestock/fowl or pets.

In the present invention, the "regulatory dendritic cell" is not particularly limited as long as it is a subset of dendritic cells that are involved in immune tolerance and have the capacity to induce regulatory T cells (for example, $CD4^+$ $CD25^+Foxp3^+$ regulatory T cells) that are induced by ALAs or ALAs and an iron compound and act to suppress the activity of potentially histotoxic T cells. The regulatory dendritic cell may be a cell derived from the patient to be treated or a cell derived from an organism other than the patient; however, it is preferably a cell derived from the patient. The regulatory dendritic cell of the present invention can be induced and isolated by, for example, treating a cell obtained from bone marrow with the immune tolerance inducing agent and GM-CSF in vitro.

The kit for inducing a regulatory dendritic cell in vitro according to the present invention comprises the immune tolerance inducing agent of the present invention and GM-CSF, and normally, a package insert stating that the kit is used for inducing regulatory dendritic cells in vitro is attached.

Examples of the allergic disease include atopic dermatitis, allergic rhinitis, allergic conjunctivitis, bronchial asthma, pollinosis, allergic gastroenteritis, food allergy, and urticaria. For example, the preventive and/or therapeutic agent for allergic disease of the present invention can be confirmed to be effective for the treatment of atopic dermatitis by the experiment using a mouse model of atopic dermatitis, which will be described in Example 5 later. As the preventive and/or therapeutic agent for allergic disease of the present invention, in particular an agent comprising ALAs and an iron compound is generally used.

Examples of the autoimmune disease can include rheumatoid arthritis, systemic lupus erythematosus, discoid lupus erythematosus, polymyositis, scleroderma, mixed connective tissue disease, Hashimoto's thyroiditis, primary myxedema, thyrotoxicosis, pernicious anemia, Good-pasture's syndrome, rapidly progressive glomerulonephritis, myasthenia gravis, pemphigus vulgaris, bullous pemphigoid, insulin-resistant diabetes, juvenile diabetes, Addison's disease, atrophic gastritis, male sterility, climacterium praecox, lens-induced uveitis, exchangeable pulse flame, multiple sclerosis, ulcerative colitis, primary biliary cirrhosis, chronic active hepatitis, autoimmune hemolytic anemia, paroxysmal hemoglobinuria, sudden thrombocytopenic purpura, and Sjogren's syndrome. For example, the preventive and/or therapeutic agent for autoimmune disease of the present invention can be confirmed to be effective for the treatment of scleroderma by an experiment using a mouse model of scleroderma.

The combination of the preventive and/or therapeutic agents for allergic disease of the present invention is not particularly limited as long as it is a combination of the preventive and/or therapeutic agent for allergic disease of the present invention and a therapeutic drug for allergic disease and a combination of ALAs, an iron compound, and a therapeutic drug for allergic disease. Allergic disease can be prevented and/or treated by administering these combinations. Examples of the therapeutic drug for allergic disease include a pharmaceutical product such as tranilast, clemastine fumarate, cyproheptadine hydrochloride, diphenhydramine, methdilamine, clemizole, and methoxyphenamine. The preventive and/or therapeutic agent for allergic disease and the preventive and/or therapeutic kit for allergic disease according to the present invention differ in the mechanism of action from existing therapeutic drugs for allergic disease. Thus, use of the combination of the preventive and/or therapeutic agents for allergic disease of the present invention can be expected to produce additive effects and, in some cases, synergistic effects.

The combination of the preventive and/or therapeutic agents for autoimmune disease of the present invention is not particularly limited as long as it is a combination of the preventive and/or therapeutic agent for autoimmune disease of the present invention and a therapeutic drug for autoimmune disease and a combination of ALAs, an iron compound, and a therapeutic drug for autoimmune disease. Autoimmune disease can be prevented and/or treated by administering these combinations. Examples of the therapeutic drug for autoimmune disease include a pharmaceutical product such as corticosteroid, cyclophosphamide, tacrolimus, mycophenolate mofetil, anti-cytokine monoclonal antibody, interferon-β, copolymer-1, sulfasalazine, hydroxychloroquine, leuflonamide, prednisone, TNFα antagonist, etanercept, and infliximab. The preventive and/or therapeutic agent for autoimmune disease and the preventive and/or therapeutic kit for autoimmune disease according to the present invention differ in the mechanism of action from existing therapeutic drugs for autoimmune disease. Thus, use of the combination of the preventive and/or therapeutic agents for autoimmune disease of the present invention can be expected to produce additive effects and, in some cases, synergistic effects.

Examples of the compound used as an active ingredient in the immune tolerance inducing agent of the present invention can include a compound represented by the formula (I) or a salt thereof (hereinafter, they are also collectively referred to as "ALAs"). ALA, also called δ-aminolevulinic acid, is represented by the formula (I) wherein $R^1$ and $R^2$ each represent a hydrogen atom, and is one type of amino acid. Examples of ALA derivatives can include compounds (other than ALA) represented by the formula (I) wherein $R^1$ represents a hydrogen atom or an acyl group; and $R^2$ represents a hydrogen atom, a linear or branched alkyl group, a cycloalkyl group, an aryl group, or an aralkyl group.

Among these ALAs, preferable examples thereof include ALA represented by the formula (I) wherein $R^1$ and $R^2$ each represent a hydrogen atom or a salt thereof. ALA, also called δ-aminolevulinic acid, is one type of amino acid. Examples of ALA derivatives can include compounds (other than ALA) represented by the formula (I) wherein $R^1$ represents a hydrogen atom or an acyl group; and $R^2$ represents a hydrogen atom, a linear or branched alkyl group, a cycloalkyl group, an aryl group, or an aralkyl group.

Examples of the acyl group in the formula (I) can include: linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl groups; and aroyl groups having 7 to 14 carbon atoms such as benzoyl, 1-naphthoyl, and 2-naphthoyl groups.

Examples of the alkyl group in the formula (I) can include linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups.

Examples of the cycloalkyl group in the formula (I) can include cycloalkyl groups having 3 to 8 carbon atoms which are saturated or may have a partially unsaturated bond, such as cyclopropyl, cyclobutyl, cyclopentyl, cyclohexyl, cycloheptyl, cyclooctyl, cyclododecyl, and 1-cyclohexenyl groups.

Examples of the aryl group in the formula (I) can include aryl groups having 6 to 14 carbon atoms such as phenyl, naphthyl, anthryl, and phenanthryl groups.

Examples of the aralkyl group in the formula (I) can include aralkyl groups whose aryl moiety is the same as those exemplified above as the aryl group and alkyl moiety is the same as those exemplified above as the alkyl group and can specifically include aralkyl groups having 7 to 15 carbon atoms such as benzyl, phenethyl, phenylpropyl, phenylbutyl, benzhydryl, trityl, naphthylmethyl, and naphthylethyl groups.

The ALA derivative is preferably a compound wherein $R^1$ is, for example, a formyl, acetyl, propionyl, or butyryl group or a compound wherein $R^2$ is, for example, a methyl, ethyl, propyl, butyl, or pentyl group. Preferable examples of combinations of $R^1$ and $R^2$ can include combinations of formyl and methyl, acetyl and methyl, propionyl and methyl, butyryl and methyl, formyl and ethyl, acetyl and ethyl, propionyl and ethyl, and butyryl and ethyl.

It is only required that ALAs should act as an active ingredient in the form of ALA of the formula (I) or its derivative in vivo. ALAs can be administered as various salts, esters, or prodrugs (precursors), which are degradable by enzymes in vivo, in order to enhance solubility according to dosage forms. Examples of the salts of ALA and its derivative can include pharmacologically acceptable acid-addition salts, metal salts, ammonium salts, and organic amine-addition salts. Examples of the acid-addition salts can include: various inorganic acid salts such as hydrochloride, hydrobromide, hydroiodide, phosphate, nitrate, and sulfate; and various organic acid-addition salts such as formate, acetate, propionate, toluenesulfonate, succinate, oxalate, lactate, tartrate, glycolate, methanesulfonate, butyrate, valerate, citrate, fumarate, maleate, and malate. Examples of the metal salts can include: various alkali metal salts such as lithium salt, sodium salt, and potassium salt; various alkaline earth metal salts such as magnesium and calcium salts; and salts of various other metals such as aluminum and zinc. Examples of the ammonium salts can include ammonium salt and alkylammonium salts such as tetramethylammonium salts. Examples of the organic amine salts can include various salts such as triethylamine salt, piperidine salt, morpholine salt, and toluidine salt. These salts may be used in the form of solution.

Of these ALAs, ALA and various esters thereof such as ALA methyl ester, ALA ethyl ester, ALA propyl ester, ALA butyl ester, and ALA pentyl ester, and their hydrochlorides, phosphates, and sulfates are desirable. Particularly preferable examples thereof can include ALA hydrochloride and ALA phosphate.

These ALAs can be produced by any method known in the art such as chemical synthesis, microbial production, or enzymatic production. Also, these ALAs may form a hydrate or a solvate and can be used alone or in appropriate combination of two or more thereof.

The iron compound may be an organic salt or an inorganic salt. Examples of the inorganic salt can include ferric chloride, iron sesquioxide, iron sulfate, and ferrous pyrophosphate. Examples of the organic salt can include: carboxylates, for example, hydroxycarboxylates including citrates such as ferrous citrate, iron sodium citrate, sodium ferrous citrate, and iron ammonium citrate; organic acid salts such as ferric pyrophosphate, iron lactate, ferrous gluconate, iron sodium diethylenetriaminepentaacetate, iron ammonium diethylenetriaminepentaacetate, iron sodium ethylene diaminetetraacetate, iron ammonium ethylene diaminetetraacetate, iron sodium dicarboxymethylglutamate, iron ammonium dicarboxymethylglutamate, ferrous fumarate, iron acetate, iron oxalate, ferrous succinate, and sodium iron succinate citrate; and heme iron, iron dextran, iron triethylenetetramine, lactoferrin iron, transferrin iron, sodium iron chlorophyllin, ferritin iron, saccharated iron oxide, and iron glycine sulfide. Among them, sodium ferrous citrate or iron sodium citrate is preferable.

These iron compounds may be used alone or as a mixture of two or more thereof. The dose of the iron compound can be 0.01 to 100 parts by mol with respect to 1 part by mol of ALAs (in terms of the dose of ALA) and is preferably 0.05 to 10 parts by mol, more preferably 0.1 to 8 parts by mol, with respect to 1 part by mol of ALAs (in terms of the dose of ALA).

For the method for inducing immune tolerance, the method for inducing a regulatory dendritic cell, the method for preventing and/or treating allergic disease, and the method for preventing and/or treating autoimmune disease according to the present invention, it is preferred to administer ALAs and an iron compound in combination. In particular, for the method for preventing and/or treating allergic disease, it is preferred to administer ALAs and an iron compound in combination. In these cases, ALAs and the iron compound can be administered either as a composition comprising them or each independently at the same time or in tandem. In the case where ALAs and the iron compound are administered each independently, it is preferred to administer them at the same time. In the case where ALAs and the iron compound are administered each independently in tandem, it is preferred to administer them so as to produce additive effects, preferably synergistic effects.

Examples of administration routes for each ingredient in the immune tolerance inducing agent, the regulatory dendritic cell inducing agent, the preventive and/or therapeutic agent for allergic disease, and the preventive and/or therapeutic agent for autoimmune disease and the kits for these agents according to the present invention can include oral administration (including sublingual administration) and parenteral administration such as nasal drip, inhalation, intravenous administration (including drip infusion), transdermal administration using patches or the like, and administration based on suppositories or forced enteral feeding using nasogastric tubes, nasoenteric tubes, gastric fistula tubes, or intestinal fistula tubes. Oral administration is preferable.

Examples of the dosage form of each ingredient in the immune tolerance inducing agent, the regulatory dendritic cell inducing agent, the preventive and/or therapeutic agent for allergic disease, and the preventive and/or therapeutic agent for autoimmune disease and the kits for these agents according to the present invention can be appropriately determined according to the administration route. Examples thereof can include injections, nasal drops, intravenous drops, tablets, capsules, fine granules, powders, solutions, liquid agents dissolved in syrups or the like, patches, and suppositories. Each ingredient in the immune tolerance inducing agent or the kit for inducing immune tolerance of the present invention may be administered for medical use as well as in the form of supplement tablets or capsules. Particularly, the form of disintegrating tablets that are rapidly disintegrable in the mouth or the form of solutions suitable for nasogastric administration is preferable for elderly people, infants, or the like who have difficulty in swallowing.

The immune tolerance inducing agent, the regulatory dendritic cell inducing agent, the preventive and/or therapeutic agent for allergic disease, and the preventive and/or therapeutic agent for autoimmune disease and the kits for these agents according to the present invention can be prepared, if necessary, by the addition of pharmacologically acceptable carriers, excipients, diluents, additives, disintegrants, binders, coating agents, lubricants, glidants, flow conditioners, flavoring agents, sweetening agents, solubilizers, solvents, gelling agents, nutrients, etc. Specific examples thereof can include water, saline, animal fat and oil, plant oil, lactose, starch, gelatin, crystalline cellulose, gum, talc, magnesium stearate, hydroxypropylcellulose, polyalkylene glycol, polyvinyl alcohol, and glycerin. In the case of preparing the agent for promoting graft survival of the present invention as an aqueous solution, it should be noted that the aqueous solution is kept from becoming alkaline, in order to prevent the degradation of ALAs. If the aqueous solution becomes alkaline, the degradation of ALAs may be prevented by the removal of oxygen.

The immune tolerance inducing agent, the regulatory dendritic cell inducing agent, the preventive and/or therapeutic agent for allergic disease, and the preventive and/or therapeutic agent for autoimmune disease and the kits for these agents according to the present invention can also be used, as described above, for humans as well as in the veterinary field including livestock/fowl or pets. The dose, administration frequency, and administration period of the immune tolerance inducing agent or the like differ depending on the age, body weight, conditions, etc., of, for example, a human subject. Examples of the dose of ALAs per adult can include 0.1 to 12 mmol/day, preferably 0.2 to 9 mmol/day, more preferably 0.3 to 6 mmol/day, further preferably 0.35 mmol/day to 4 mmol/day in terms of moles of ALA. Examples of the administration frequency can include one or more dosages per day and continuous administration using drip infusion or the like. The administration period may be determined by a pharmacologist in this technical field or a clinician according to existing methods.

Hereinafter, the present invention will be described more specifically with reference to Examples. However, the technical scope of the present invention is not intended to be limited to these examples.

Example 1

Dendritic cells (DC) were prepared using ALA and SFC, and an evaluation was made as to whether the cells actually prepared induced regulatory T cells and had an equivalent function to that of regulatory DC induced by transforming growth factor-β (TGF-β) and IL-10, which are inflammation inhibitory cytokines secreted by regulatory T cells.
[Induction of Dendritic Cells by the Addition of ALA to Cells Obtained from Bone Marrow]

Bone marrow was extracted from an 8-week-old A/J(H2-$K^K$) mouse. After removing erythrocytes by hemolysis treatment, the resulting cells were seeded in a culture dish. The cells were then cultured in an RPMI-based medium (hereinbelow, written as an RPMI medium), and from the second day, 100 µM ALA hydrochloride and 50 µM SFC were administered in conjunction with 10 ng/ml cytokine GM-CSF, and culture was continued for three days. The medium was then exchanged for a fresh RPMI medium (containing 10 ng/ml GM-CSF, 100 µM ALA hydrochloride, and 50 µM SFC), and the cells were further cultured for three days, and then harvested. Hereinbelow, the cells obtained by the above culture method will be referred to as BM-DC$_{ALA}$.
[Induction of Mature Dendritic Cell-Like Cells (BM-DCcon) and Tolerogenic Dendritic Cell-Like Cells (BM-DCreg) as a Control Group]

As a control group, BM-DCcon induced from bone marrow cells (as with mature dendritic cells, known to have the capacity to activate effector T cells, which evoke immune reaction) and BM-DCreg induced from bone marrow cells (as with regulatory dendritic cells, known to have the capacity to activate regulatory T cells, which suppress immune reaction) were prepared. BM-DCcon cells were cultured using cells which had been seeded in a culture dish by the technique similar to the above for five days in an RPMI medium with the addition of GM-CSF (10 ng/ml) and IL-4 (10 ng/ml). Subsequently, a lipopolysaccharide (LPS) antigen was added at 1 µg/ml to a fresh medium having the same composition, in which the cells were further cultured for two days. The reason for administration of LPS is that the presence of a substance serving as an antigen is necessary for the maturation of dendritic cells. Similarly to the above technique, BM-DCreg cells were cultured using cells which had been seeded in a culture dish by the technique similar to the above for seven days in an RPMI medium with the addition of GM-CSF (20 ng/ml), IL-10 (20 ng/ml), and TGF-β (20 mg/ml).
[Investigation on Whether or not the Cells Thus Obtained are Dendritic Cells]

As a premise, whether or not BM-DC$_{ALA}$, BM-DCcon, and BM-DCreg obtained by the three techniques were dendritic cells was investigated. That is, the cells were stained by two dendritic cell markers, i.e., CD11b and CD11c, and the numbers of double-positive cells (i.e., dendritic cells) were compared using a flow cytometer. The results are shown in FIG. 1 (the leftmost column). As a result, it was found that the majority of the cell population was both CD11b and CD11c positive in all groups, revealing that the cells were induced into dendritic cells. Subsequently, the function of the dendritic cells thus prepared was studied.

Example 2

Expression of the Dendritic Cell-Specific Surface Markers

The expression of the dendritic cell-specific surface marker was examined to see if the dendritic cells induced by the addition of ALA had characteristics of mature dendritic cells or tolerogenic dendritic cells. That is, the expression of the mature dendritic cell markers, i.e., CD80, CD86, CD40, and I-A.I-E (MHC class II), was analyzed by a flow cytometer. The results are shown in FIG. 1 (the four columns on the right side). As a result, as has been known, it was found that the mature dendritic cell markers were expressed in BM-DCcon, whereas the expression of those markers was lower in BM-DCreg than in BM-DCcon. Compared to the above, the expression of each mature dendritic cell marker in BM-DC$_{ALA}$ was as low as that in BM-DCreg. That is, it was suggested that dendritic cells closely resembling BM-DCreg were successfully prepared by the addition of ALA.

Example 3

Expression of the Immune Related Genes

Figure 2:
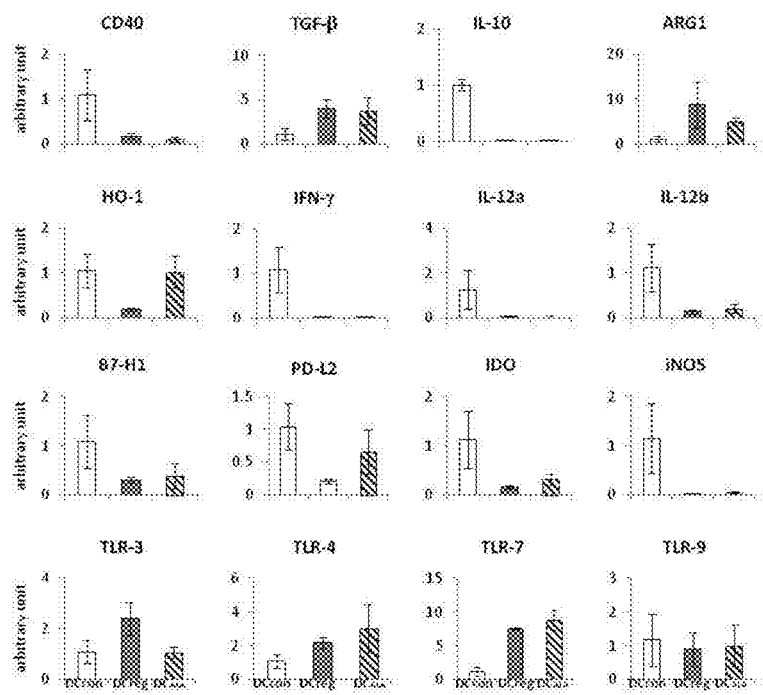
FIG. 2 is a set of diagrams showing the results of the expression of the dendritic cell-specific immune related genes.

It was studied whether or not the dendritic cells induced by the addition of ALA expressed a gene similar to that expressed in mature dendritic cells or tolerogenic dendritic cells. That is, mRNA was extracted from BM-DC$_{ALA}$, BM-DCcon, and BM-DCreg and the expression of a gene involved in immune induction or immune suppression was examined by RT-PCR. The results are shown in FIG. 2. As a result, BM-DC$_{ALA}$ exhibited a tendency similar to that of BM-DCreg with respect to many genes. For example, the expression level of CD40, which is a mature dendritic cell marker, was low, while the expression level of TGF-β was high in BM-DC$_{ALA}$. Meanwhile, BM-DC$_{ALA}$ exhibited a gene expression similar to that of BM-DCcon with respect to genes such as HO-1.

That is, it was shown that the properties did not completely match but were similar between BM-DCreg and BM-DC$_{ALA}$.

Example 4

Investigation of the Immune Tolerance Capacity of BM-DC$_{ALA}$ by the MLR Method It was investigated using the Mixed Lymphocyte Reaction (MLR) method whether or not BM-DC$_{ALA}$ suppressed T cell activation similarly to BM-DCreg, in other words, induced immune tolerance in which effector T cell proliferation is inhibited by the induction of regulatory T cells. In the living body, mature dendritic cells that have recognized foreign bodies serving as antigens present those antigens to T cells. Upon recognition of such antigens, T cells undergo explosive proliferation. Also in vitro, when T cells and mature DC are mixed-cultured with an antigen, proliferation of T cells is observed. In light of this, the activity of mature DC can be measured by measuring this rate of T cell proliferation (MLR method). It is also known that when mature DCs of different lineages are mixed with T cells, proliferation is still observed even in the absence of an antigen.

(Investigation of the Inhibitory Effect of BM-DC$_{ALA}$ on Effector T Cell Proliferation)

Figure 3:
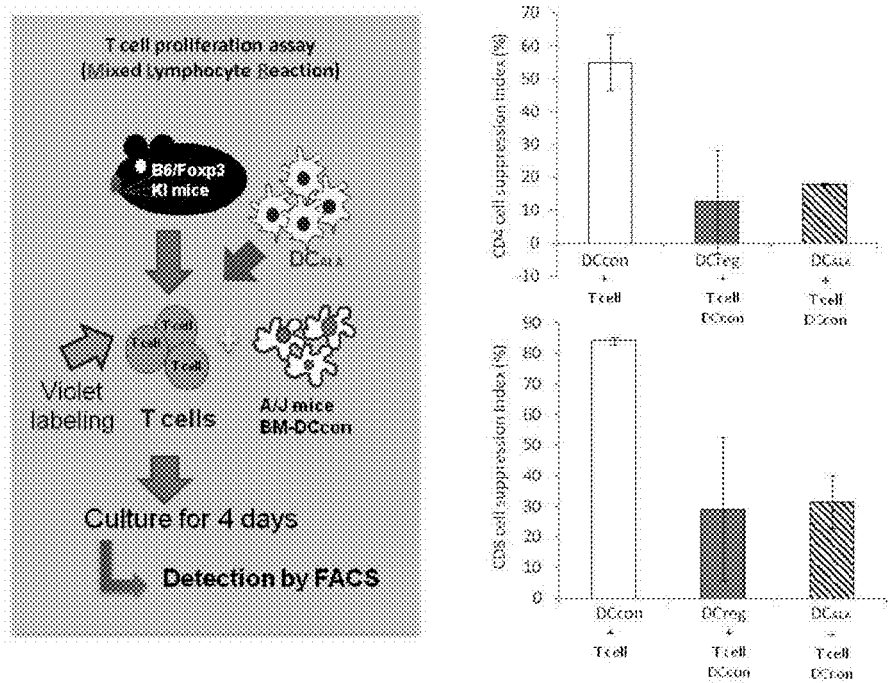
FIG. 3 is a set of diagrams showing the results of the inhibitory effect of dendritic cells (BM-$DC_{ALA}$) induced by adding ALA to the cells obtained from bone marrow on effector T cell proliferation.

It was investigated using the MLR method whether or not the effector T cell proliferation-inducing capacity, which is a function of mature dendritic cells, could be suppressed by the presence of BM-DC$_{ALA}$. Using a nylon fiber column, T cells were separated from the spleen of a B6-strain mouse and stained purple with the Violet Cell Proliferation Kit supplied by Molecular Probes. T cells were then cultured at 2×10$^5$ cells/well with BM-DCcon (used in place of mature dendritic cells) of the A/J mouse at 1×10$^4$ cells/well for four days in an MPRI medium. At this time, BM-DCreg or BM-DC$_{ALA}$ was added at 2×10$^4$ cells/well. In order to study the degree of proliferation of effector T cells after culturing, the proportion of effector T cells (CD4 and CD8-positive) in the total T cells (purple) was measured by a flow cytometer. It is to be noted that although regulatory T cells are also CD4-positive, their proportion in the total T cells is negligibly small. The results are shown in FIG. 3. As a result, compared to a negative control two-cell mixed culture of BM-DCcon and T cells, the proportion of each of the CD4-positive and CD8-positive T cells was decreased by a three-cell mixed culture of BM-DCcon, T cells, and BM-DC$_{ALA}$. That is, BM-DC$_{ALA}$ suppressed the effector T cell proliferation. This suppressive capacity was equivalent to that of BM-DCreg, which is known to have an effector T cell proliferation-suppressive capacity.

(Investigation of the Capacity of BM-DC$_{ALA}$ to Induce Regulatory T Cells)

Figure 4:
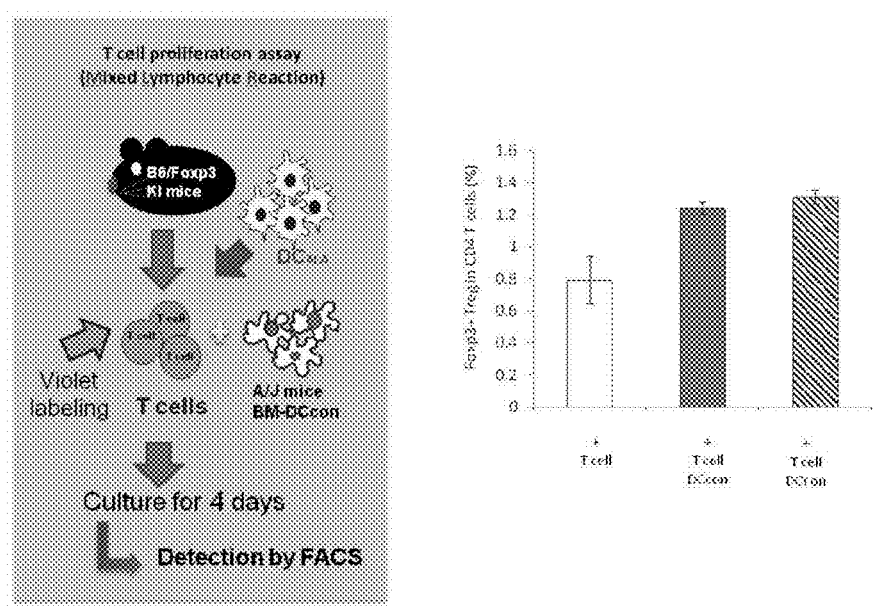
FIG. 4 is a set of diagrams showing the results of the capacity of BM-$DC_{ALA}$ to induce regulatory T cells.

It was investigated whether or not BM-DC$_{ALA}$ had the regulatory T cell-inducing capacity, which is the function of tolerogenic dendritic cells. T cells were obtained from a B6-strain mouse in which the FoxP3 gene is replaced by the GFP gene and stained by a similar technique to that used in Example 4, and then mixed-cultured with BM-DCcon. At this time, BM-DCreg or BM-DC$_{ALA}$ was added. The proportion of GFP-positive cells present in the total T cells (purple) was examined. The results are shown in FIG. 4. As a result, as with BM-DCreg, the proportion of GFP-positive cells in the T cell population was increased by the addition of BM-DC$_{ALA}$. That is, it was suggested that BM-DC$_{ALA}$ induced regulatory T cells.

Figure 5:
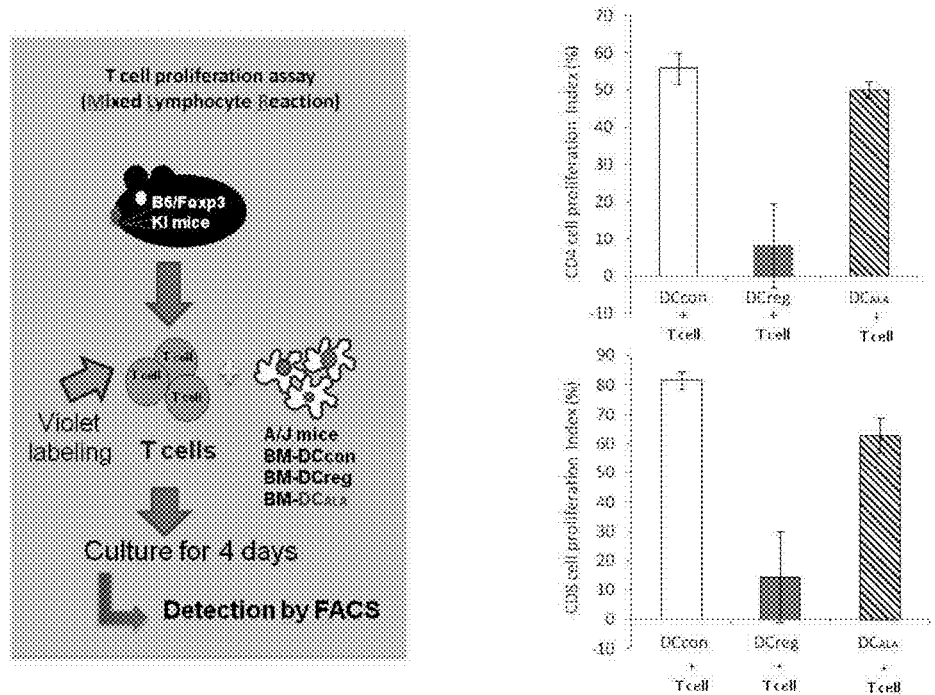
FIG. 5 is a set of diagrams showing the results of the inhibitory effect of BM-$DC_{ALA}$ on effector T cell proliferation.

Because there is no antibody for FoxP3 that is suitable for a flow cytometer, the knock-in mouse was used as a means for confirming the expression of FoxP3 by a flow cytometer. When a regulatory T cell differentiation signal signals the expression of FoxP3, GFP is expressed instead. By measuring the proportion of GFP-positive cells in the purple-stained T cell population, the proportion of (supposedly) FoxP3-positive cells, in other words, the inducing capacity, can be assayed. Also, it has been confirmed that although the B6-strain mouse shown in FIG. 3 and FIG. 5 is also a GFP knock-in mouse, no influence was exerted on either CD4 or CD8, both of which are parameters of interest.

(Investigation of the Inhibitory Effect on Effector T Cell Proliferation)

It was investigated whether or not BM-DC$_{ALA}$ behaved in a similar manner to BM-DCreg in terms of the inhibitory effect on effector T cell proliferation when BM-DC$_{ALA}$ alone was mixed-cultured with T cells. T cells were obtained from a B6-strain mouse and stained by a similar technique to that used in Example 4, and then mixed-cultured with BM-DC$_{ALA}$. After culturing, the proportion of effector T cells in the total T cells (stained purple) was measured by a flow cytometer. The results are shown in FIG. 5. As a result, the proportion of effector T cells (CD4 and CD8-positive) was equivalent to that resulting from a two-cell mixed culture of BM-DCcon and T cells. Meanwhile, unlike the mixed culture of BM-DCcon or BM-DC$_{ALA}$ with T cells, the proportion of effector T cells was low in a two-cell mixed culture of BM-DCreg and T cells. That is, BM-DC$_{ALA}$ alone does not have an inhibitory effect on effector T cell proliferation, but rather acts like mature dendritic cells by promoting the proliferation. By the above results, it was suggested that BM-DC$_{ALA}$ cells were not perfectly identical to BM-DCreg.

(Investigation of the Capacity of BM-DC$_{ALA}$ Alone to Induce Regulatory T Cells)

Figure 6:
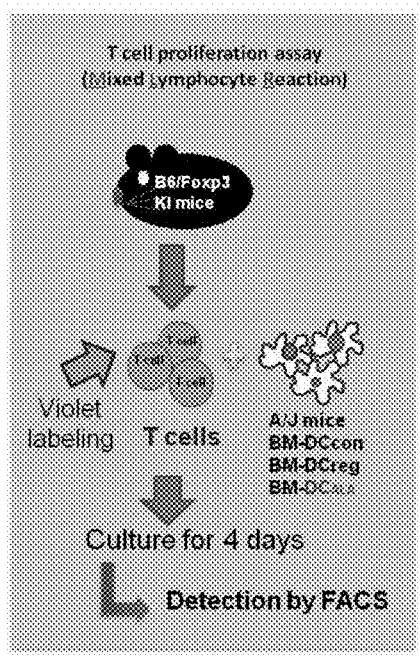
FIG. 6 is a set of diagrams showing the results of the capacity of BM-$DC_{ALA}$ alone to induce regulatory T cells.
Figure 6:
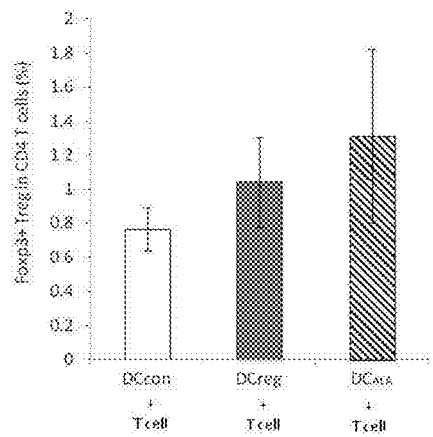

It was investigated whether or not BM-DC$_{ALA}$ behaved in a similar manner to BM-DCreg in terms of the induction of regulatory T cells when BM-DC$_{ALA}$ alone was mixed-cultured with T cells. T cells were obtained from a B6-strain mouse in which the FoxP3 gene is replaced by the GFP gene and stained by a similar technique to that used in Example 4, and then mixed-cultured with BM-DC$_{ALA}$. After culturing, the proportion of GFP-positive cells present in the total T cells (stained purple) was examined. The results are shown in FIG. 6. As a result, as with BM-DCreg, the proportion of GFP-positive cells in the T cell population was increased by the addition of BM-DC$_{ALA}$. That is, it was suggested that BM-DC$_{ALA}$ induced regulatory T cells even by itself.

From the results shown in Examples 1 to 4 above, with respect to the expression of the cell surface molecules in BMDC induced by ALA and SFC, suppression of T cell proliferation, function to increase Treg, and the like that were examined in vitro, results similar to those obtained with regulatory DC induced by TGF-β and IL-10 were successfully obtained.

Example 5

Preparation of an Atopic Mouse Model

A 10-week-old male NC/Nga strain mouse was used. As the allergen, 2,4,6-trinitrochlorobenzene (TNCB) was used to cause atopic symptoms. On Day 0, the hair in the chest, stomach, and back was shaved and 2% TNCB dissolved in ethanol:acetone (4:1) and 4% sodium dodecyl sulfate (SDS) were added dropwise in an amount of 150 μl (50 μl on the chest, 50 μl on the stomach, and 50 μl on the back). SDS was administered to disrupt the skin barrier against allergens.

Subsequently, on days 4, 11, and 18, only 1% TNCB, without SDS, was added dropwise.

[Administration of an Immune Tolerance Inducing Agent]

ALA+SFC were orally administered everyday via a gastric tube. At this time, two conditions were set with regard to concentration, which were: ALA hydrochloride (100 mg/kg)+SFC (115 mg/kg) and ALA hydrochloride (10 mg/kg)+SFC (11.5 mg/kg).

[Symptom Improvement Effects of ALA+SFC]

Figure 7:
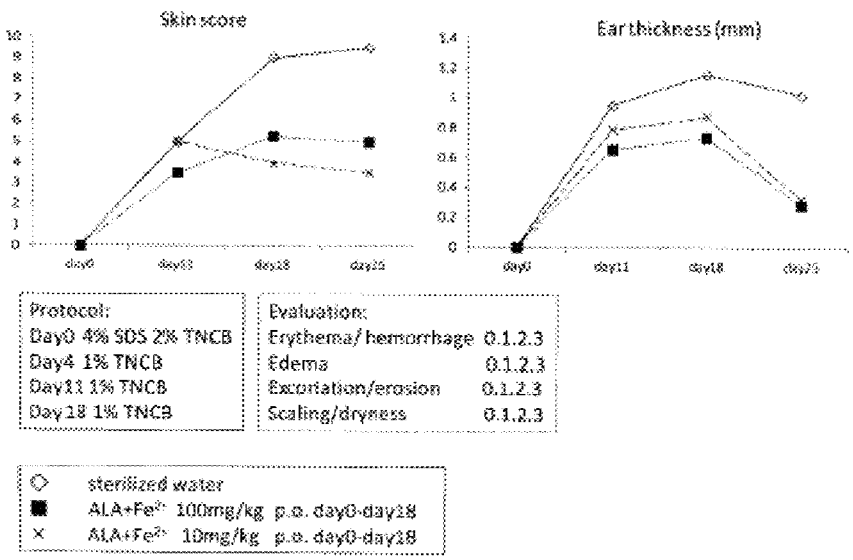
FIG. 7 is a set of diagrams showing the symptom improvement effect of the immune tolerance inducing agent of the present invention in an atopic mouse model.

As the atopic symptom evaluation system, the dermatitis scoring and auricula thickness were used. The former is judgment of the symptoms of dermatitis by visual observation. The skin damage in the back and both ears was scored based on the four criteria, which were erythema/hemorrhage, edema, excoriation/erosion, and scab/dryness, and the sum of the score of each symptom was calculated. The grade is classified into 0 (no symptoms), 1 (mild), 2 (moderate), and 3 (serious). On days 11, 18, and 25, scoring was performed. The results are shown in FIG. 7 (left). As to the auricula thickness, both ears of a sacrificed mouse were fixed by immersing in 10% neutral formalin for 24 hours at 4° C. Subsequently, the tissues were fixed in paraffin and sliced into a thickness of 4 µm. The resulting sections were stained with an H & E solution and the thickness was measured by observation under a microscope. Similarly, the auricula thickness was also scored on days 11, 18, and 25. The results are shown in FIG. 7 (right). Also, the photographs of the mice of respective administration groups on day 18 are shown in FIG. 8.

Figure 8:
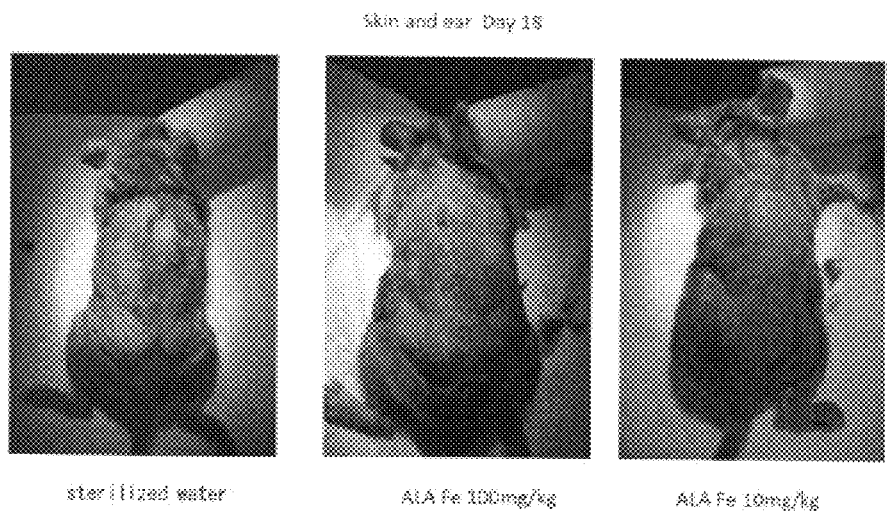
FIG. 8 is a set of photographs showing the symptom improvement effect of the immune tolerance inducing agent of the present invention in an atopic mouse model.

As understood from FIGS. 7 and 8, as a result of scoring dermatitis in the sterilized water-administered group, ALA (100 mg/kg)+SFC (115 mg/kg)-administered group, and ALA (10 mg/kg)+SFC (11.5 mg/kg)-administered group on days 11, 18, and 25, compared to the sterilized water-administered group, marked improvement was observed in the ALA (100 mg/kg)+SFC (115 mg/kg)-administered group and ALA (10 mg/kg)+SFC (11.5 mg/kg)-administered group. Similarly, as a result of measuring the auricula thickness, compared to the sterilized water-administered group, marked improvement was observed in the ALA (100 mg/kg)+SFC (115 mg/kg)-administered group and ALA (10 mg/kg)+SFC (11.5 mg/kg)-administered group.

Example 6

Preparation of a Pathological Model of Scleroderma

As a donor, a B10.D2 female (7 to 8-week-old) wild-type mouse was used, and as a recipient, a Rag-2/Balb/c female (7 to 8-week-old) immunodeficient mouse was used. A pathological mouse model of scleroderma was prepared by injecting (transplanting) the spleen cells of the donor mouse into the recipient at $5 \times 10^7$ cells or $4 \times 10^7$ cells in each group. Since the recipient is immunodeficient, rejection reaction does not occur on the recipient side and the spleen cells transplanted from the donor are not eliminated by the immune system on the recipient side; however, given that the recipient per se is perceived as a foreign body by the lymphocytes contained in the spleen cells transplanted from the donor, donor-derived lymphocytes attack the whole body of the recipient. The resulting reaction is manifested as symptoms such as systemic inflammation, tissue fibrosis, and diffuse systemic sclerosis, which closely resemble human sclerosis (pachyderma). Therefore, the mouse thus prepared can be used as a pathological model of scleroderma.

[Administration of an Immune Tolerance Inducing Agent]

From right after transplantation of the donor's spleen cells, ALA hydrochloride 100 mg/kg+SFC 157 mg/kg (hereinbelow, expressed as "ALA") were administered once daily for nine weeks via a gastric tube.

Example 7

Effect of ALA Administration on the Body Weight and Survival Period

Figure 9:
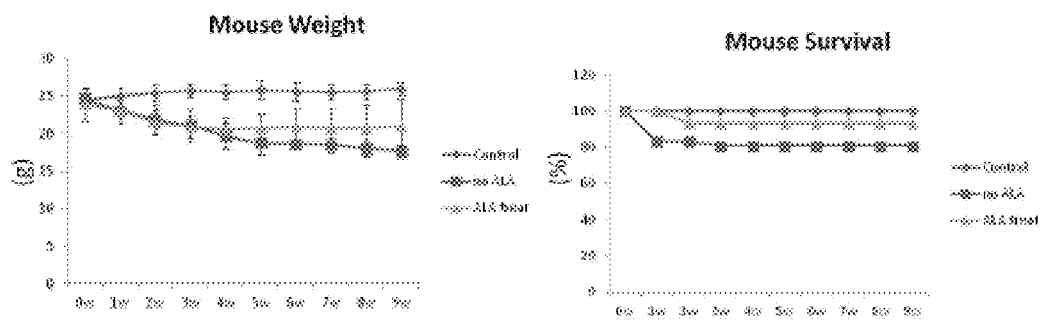
FIG. 9 is a set of diagrams showing the effect of ALA administration to a pathological mouse model of scleroderma on the body weight and survival period.
Figure 10:
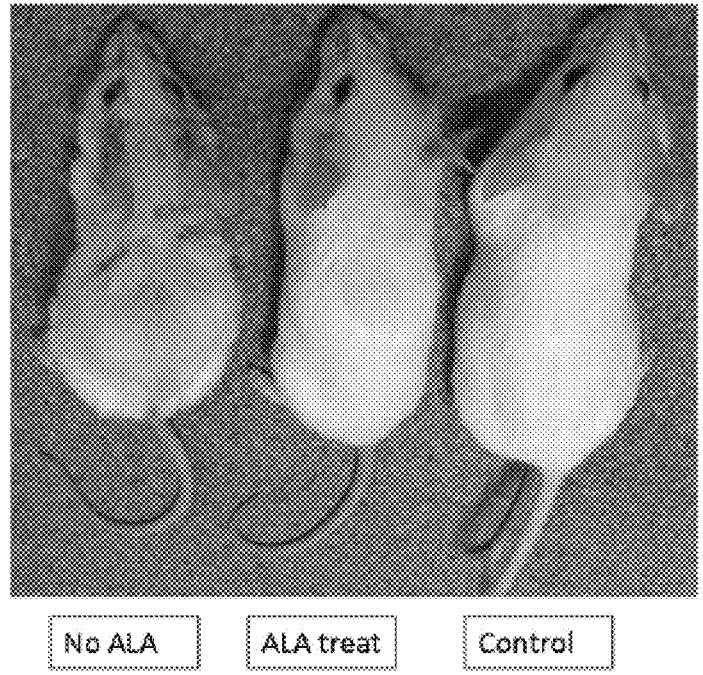
FIG. 10 is a photograph showing the appearance of a pathological mouse model of scleroderma with ALA administration.

It was investigated whether or not body weight decrease caused by the development of scleroderma was alleviated by ALA or the survival period was prolonged. As a result, as shown in FIG. 9, there was a tendency of suppression of body weight decrease by ALA administration. Also, there was a tendency of high survival rate up to nine weeks by ALA administration. Also, the typical appearance of each group is shown in FIG. 10. Alleviation of hair loss by ALA administration can be observed. Also, control is the data of a Rag-2/Balb/c female (7 to 8-week-old) immunodeficient mouse that does not receive transplantation of donor mouse-derived spleen cells. As described above, the symptom alleviating effect of ALA administration on scleroderma was observed.

Example 8

Effect of ALA Administration on Tissue (Tissue Staining)

It was determined whether the symptoms of scleroderma such as fibrosis and accumulation of immune cells (inflammation) were alleviated by ALA administration by staining the tissues derived from the mouse model. In order to observe the condition of inflamed ear, skin, kidney, liver, and lung, sections were prepared from respective organs and subjected to HE staining for confirmation of T cell accumulation, and to Masson staining for staining of collagen-containing connective tissues. Under three conditions of before cell transplantation (Naive), non-ALA administration at week 6, and ALA administration at week 6, the HE-stained sections and Masson-stained section were observed at four magnifications of ×40, ×100, ×200, and ×400 to determine whether the symptoms were alleviated by ALA administration.

[Ear]

Figure 11:
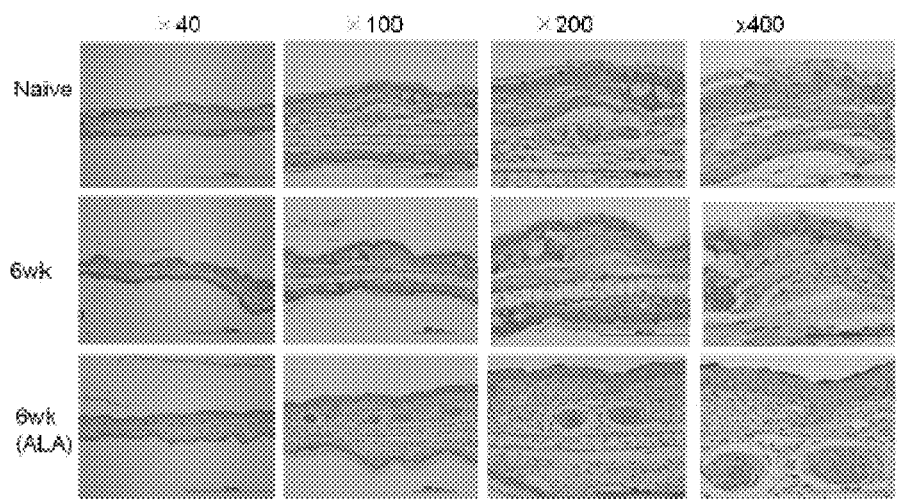
FIG. 11 is a set of diagrams showing the results of the observation of the HE-stained section of the ear of a pathological mouse model of scleroderma with ALA administration.
Figure 12:
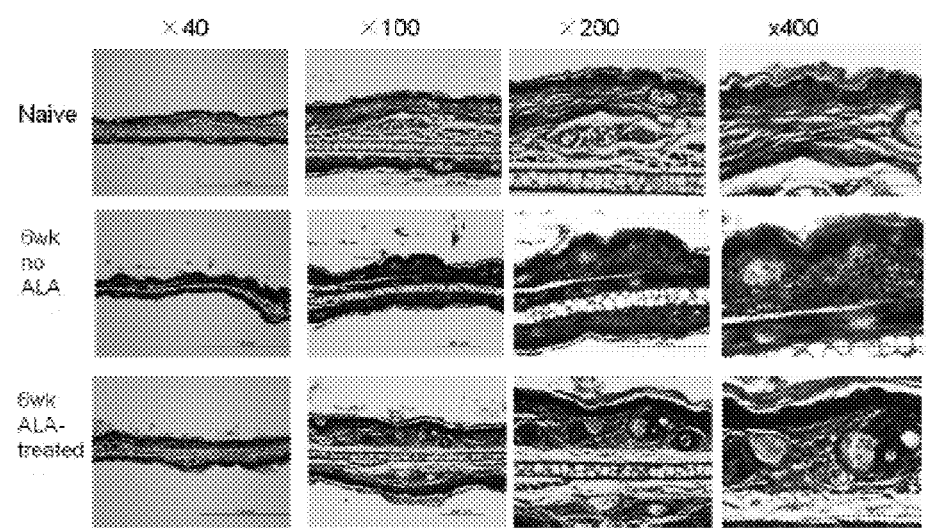
FIG. 12 is a set of diagrams showing the results of the observation of the Masson-stained section of the ear of a pathological mouse model of scleroderma with ALA administration.

The results of the observation of the HE-stained sections are shown in FIG. 11. As a result, there was no major difference in the findings of the HE-stained sections with ALA administration (comparison between the middle and bottom rows). Similarly, the results of the observation of the Masson-stained sections are shown in FIG. 12. As a result, collagen accumulation (indicated by the density of a darkly stained part) was suppressed to a greater extent in the ALA administration group than in the non-administration group (comparison between the middle and bottom rows).

[Skin]

Figure 13:
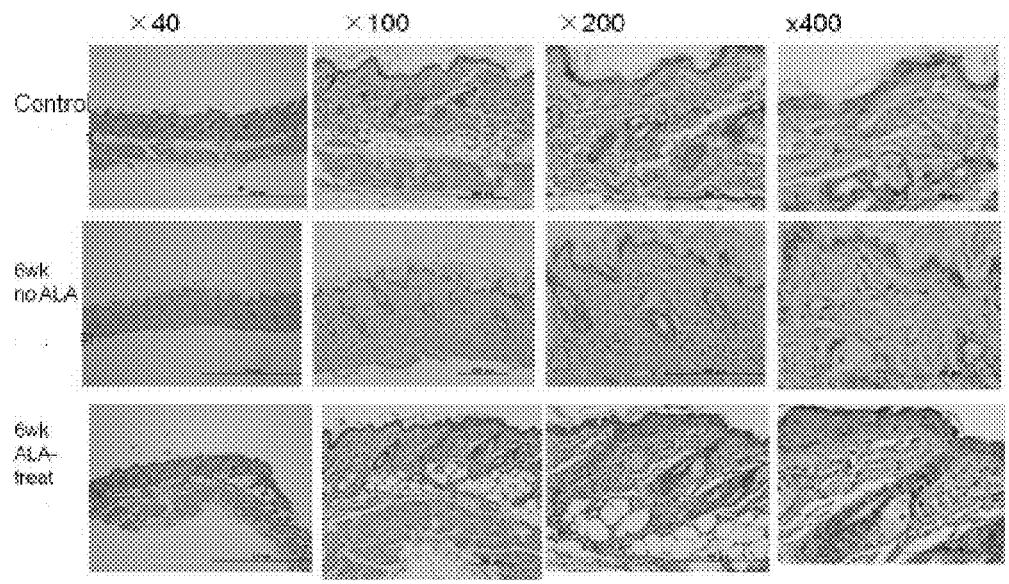
FIG. 13 is a set of diagrams showing the results of the observation of the HE-stained section of the skin of a pathological mouse model of scleroderma with ALA administration.
Figure 14:
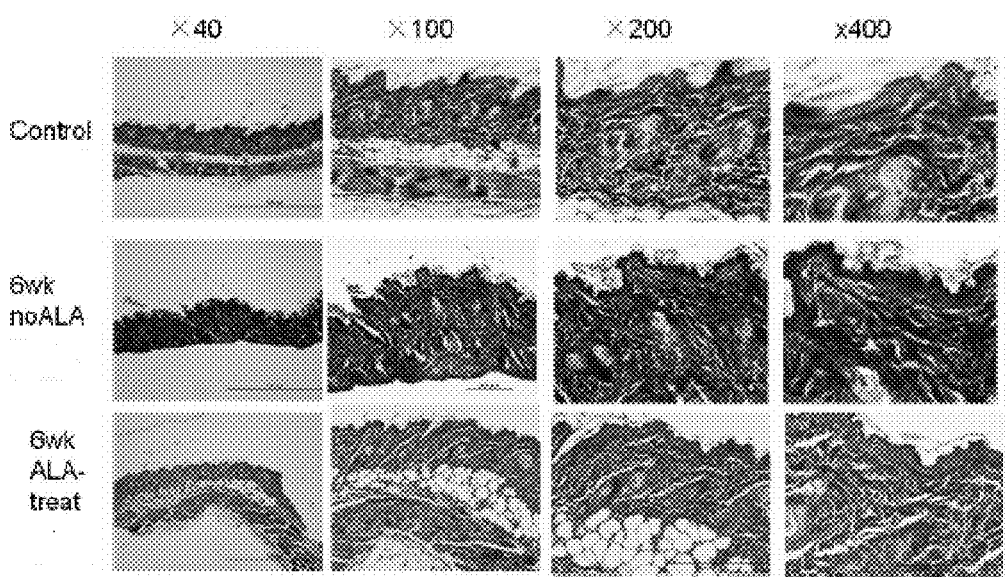
FIG. 14 is a set of diagrams showing the results of the observation of the Masson-stained section of the skin of a pathological mouse model of scleroderma by ALA administration.

Skin fibrosis is one of the most typical symptoms of scleroderma. The results of the observation of the HE-stained sections are shown in FIG. 13. As a result, there was no major difference in the findings of the HE-stained sections with ALA administration (comparison between the middle and bottom rows). Similarly, the results of the observation of the Masson-stained sections are shown in FIG. 14. As a result, collagen accumulation was suppressed to a greater extent in the ALA administration group than in the non-administration group (comparison between the middle and bottom rows).

[Vicinity of the Renal Cortex]

Figure 15:
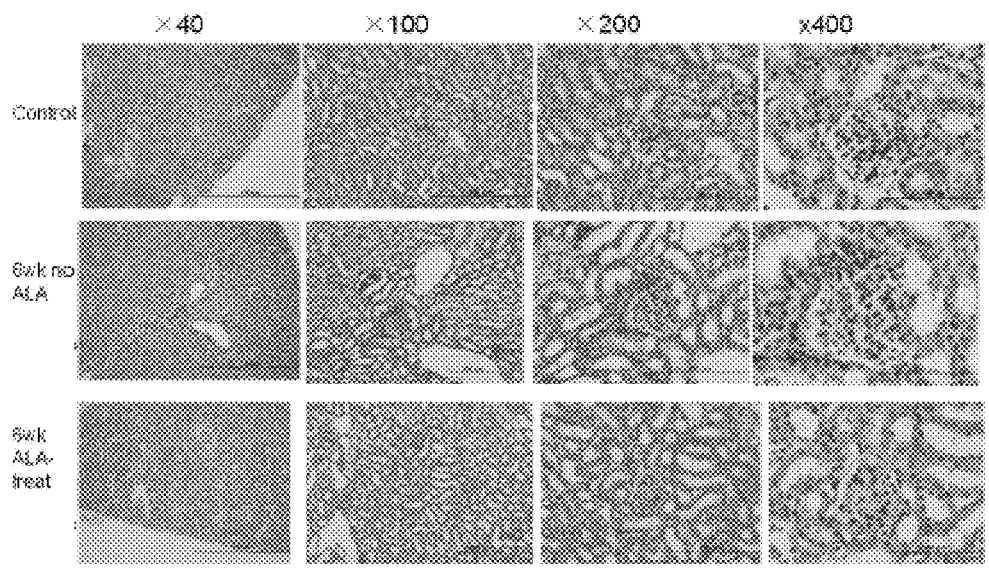
FIG. 15 is a set of diagrams showing the results of the observation of the HE-stained section of the vicinity of the renal cortex of a pathological mouse model of scleroderma with ALA administration.
Figure 16:
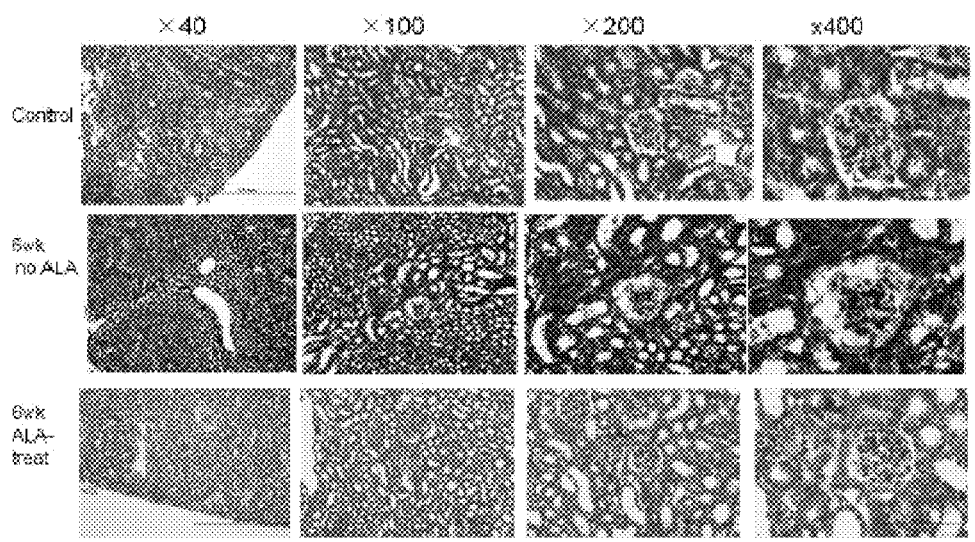
FIG. 16 is a set of diagrams showing the results of the observation of the Masson-stained section of the vicinity of the renal cortex of a pathological mouse model of scleroderma with ALA administration.

The results of the observation of the HE-stained sections are shown in FIG. 15. As a result, there was no major difference in the findings of the HE-stained sections with ALA administration (comparison between the middle and bottom rows). Similarly, the results of the observation of the Masson-stained sections are shown in FIG. 16. As a result, collagen accumulation was suppressed to a greater extent in the ALA administration group than in the non-administration group (comparison between the middle and bottom rows).

[Vicinity of the Renal Medulla]

Figure 17:
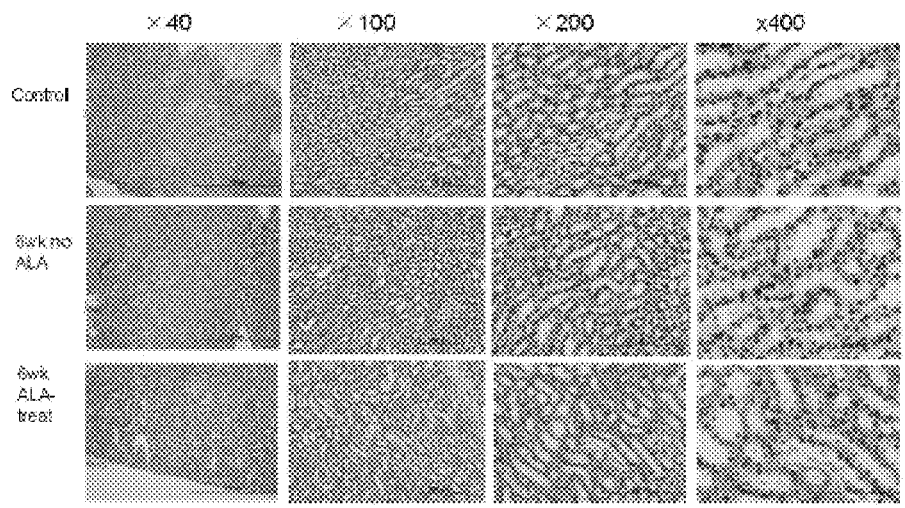
FIG. 17 is a set of diagrams showing the results of the observation of the HE-stained section of the vicinity of the renal medulla of a pathological mouse model of scleroderma with ALA administration.
Figure 18:
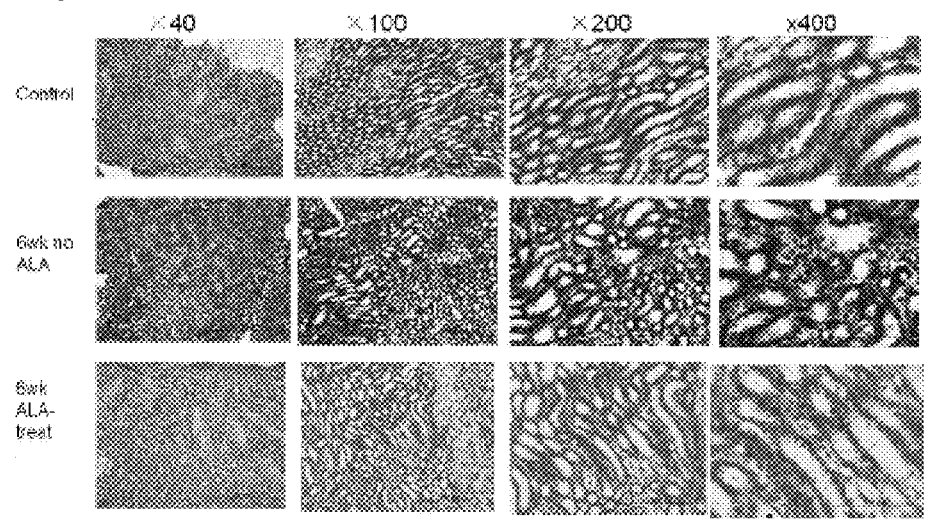
FIG. 18 is a set of diagrams showing the results of the observation of the Masson-stained section of the vicinity of the renal medulla of a pathological mouse model of scleroderma with ALA administration.

The results of the observation of the HE-stained sections are shown in FIG. 17. As a result, there was no major difference in the findings of the HE-stained sections with ALA administration (comparison between the middle and bottom rows). Similarly, the results of the observation of the Masson-stained sections are shown in FIG. 18. As a result, collagen accumulation was suppressed to a greater extent in the ALA administration group than in the non-administration group (comparison between the middle and bottom rows).

[Liver]

Figure 19:
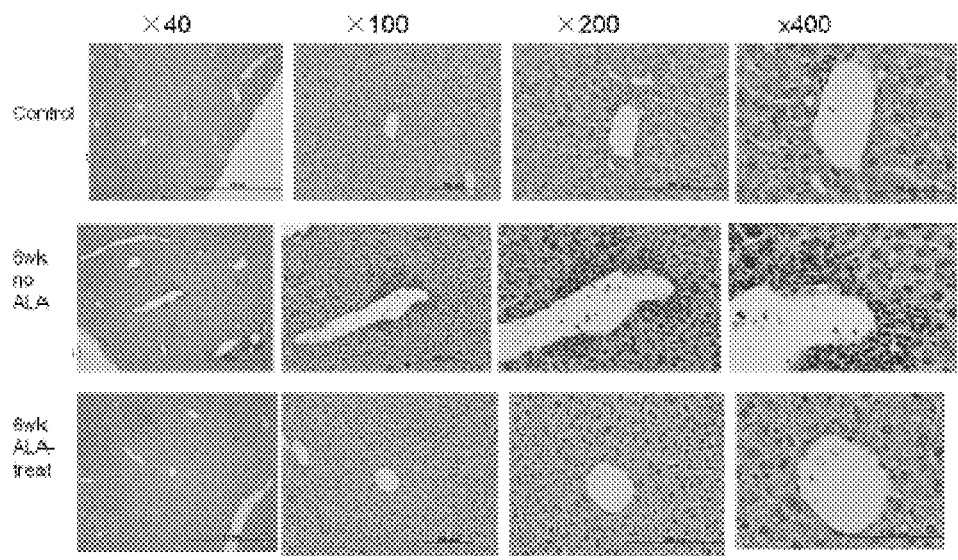
FIG. 19 is a set of diagrams showing the results of the observation of the HE-stained section of the liver of a pathological mouse model of scleroderma with ALA administration.
Figure 20:
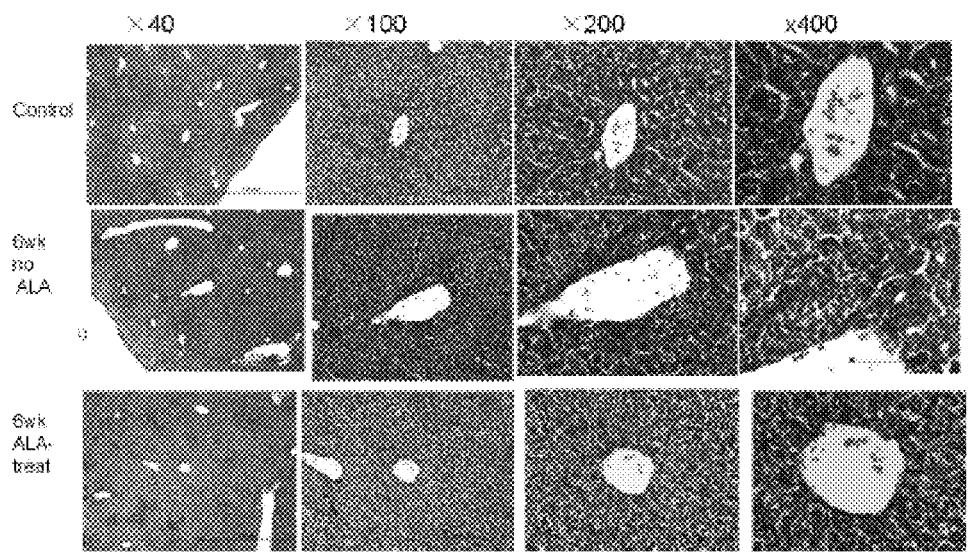
FIG. 20 is a set of diagrams showing the results of the observation of the Masson-stained section of the liver of a pathological mouse model of scleroderma with ALA administration.

The results of the observation of the HE-stained sections are shown in FIG. 19. As a result, cell accumulation was observed in the non-ALA administration group, but not in the ALA administration group in the HE-stained sections (comparison between the middle and bottom rows). Similarly, the results of the observation of the Masson-stained sections are shown in FIG. 20. As a result, there was no major difference in the findings with ALA administration (comparison between the middle and bottom rows).

[Lung]

Figure 21:
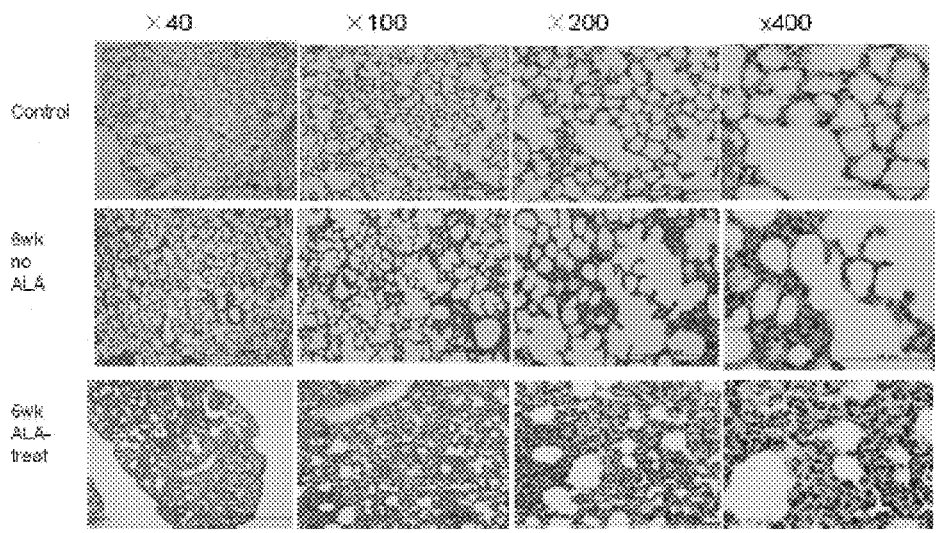
FIG. 21 is a set of diagrams showing the results of the observation of the HE-stained section of the lung of a pathological mouse model of scleroderma with ALA administration.
Figure 22:
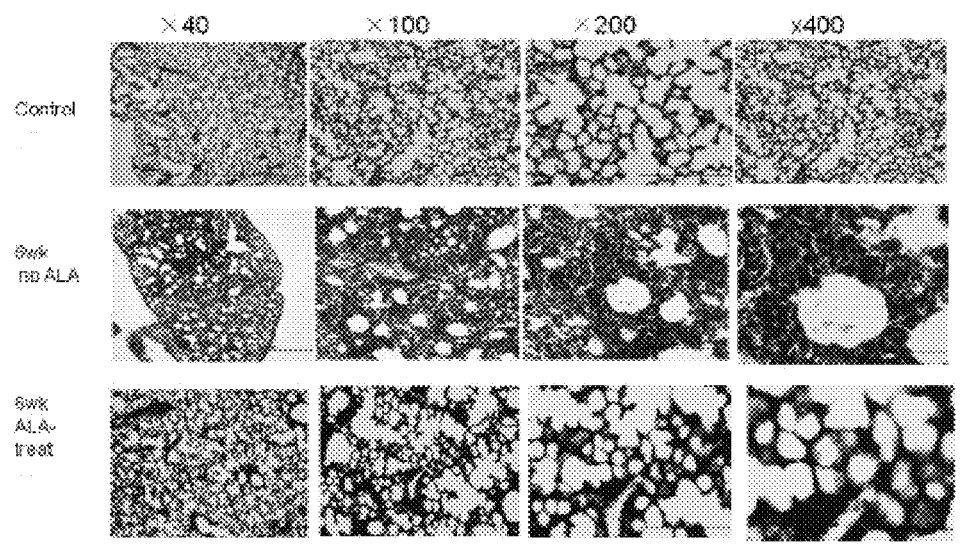
FIG. 22 is a set of diagrams showing the results of the observation of the Masson-stained section of the lung of a pathological mouse model of scleroderma with ALA administration.

The results of the observation of the HE-stained sections are shown in FIG. 21. As a result, there was no major difference in the findings of the HE-stained sections with ALA administration (comparison between the middle and bottom rows). Similarly, the results of the observation of the Masson-stained sections are shown in FIG. 22. As a result, there was no major difference in the findings with ALA administration (comparison between the middle and bottom rows).

Example 9

Effect of ALA Administration on Tissues (Gene Expression)

It was determined whether the symptoms of scleroderma such as fibrosis and inflammation were suppressed by ALA administration by detecting the expression of various marker genes in the tissues derived from the mouse model on three, six, and nine weeks after ALA administration. Using mRNA extracted from the skin, kidney, and spleen tissues by the RNeasy mini kit, the expression of genes involved in inflammation, fibrosis, and the like was examined by RT-PCR. As a control, a Balb/c male (7 to 8-week-old) mouse was used.

As the marker gene, the expression of the HO-1 (antioxidant protein, assumed to induce regDC) gene, TGF-β (inflammation inhibitory cytokine) gene, IFN-γ (ambiguous cytokine having both inflammation promoting and suppressing actions) gene, Collagen-1 (fibrosis marker) gene, α-SMA (fibrosis marker) gene, IL-6 (inflammatory cytokine) gene, osteopontin (OPN) (inflammatory cytokine) gene, IL-21 (known to be produced in a large quantity in autoimmune disease) gene, TNF-α (inflammatory cytokine) gene, IL-10 (inflammation inhibitory cytokine) gene, and FoxP3 (inhibitory T cell marker) gene was examined.

[Skin]

Figure 23:
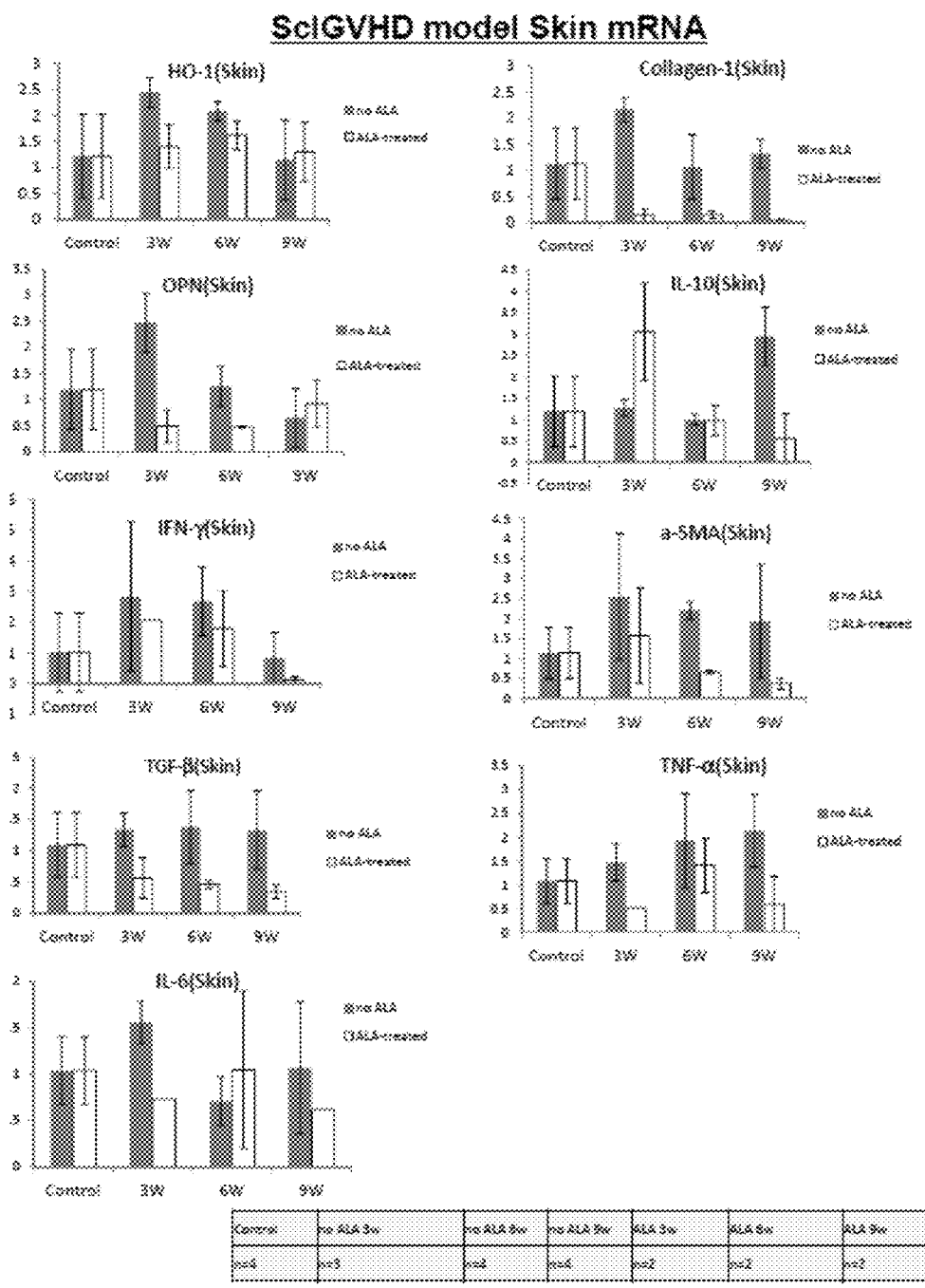
FIG. 23 is a diagram showing the results of the expression of marker genes in the skin of a pathological mouse model of scleroderma with ALA administration.

Skin fibrosis is one of the most typical symptoms of scleroderma. The results of the skin are shown in FIG. 23. In the skin, a marked reduction in collagen-1 (top right in FIG. 23) and α-SMA (right, third from the top, in FIG. 23), both of which are fibrosis markers, by ALA administration was observed, suggesting that ALA administration alleviated fibrosis, which is a symptom of scleroderma.

[Spleen]

Figure 24:
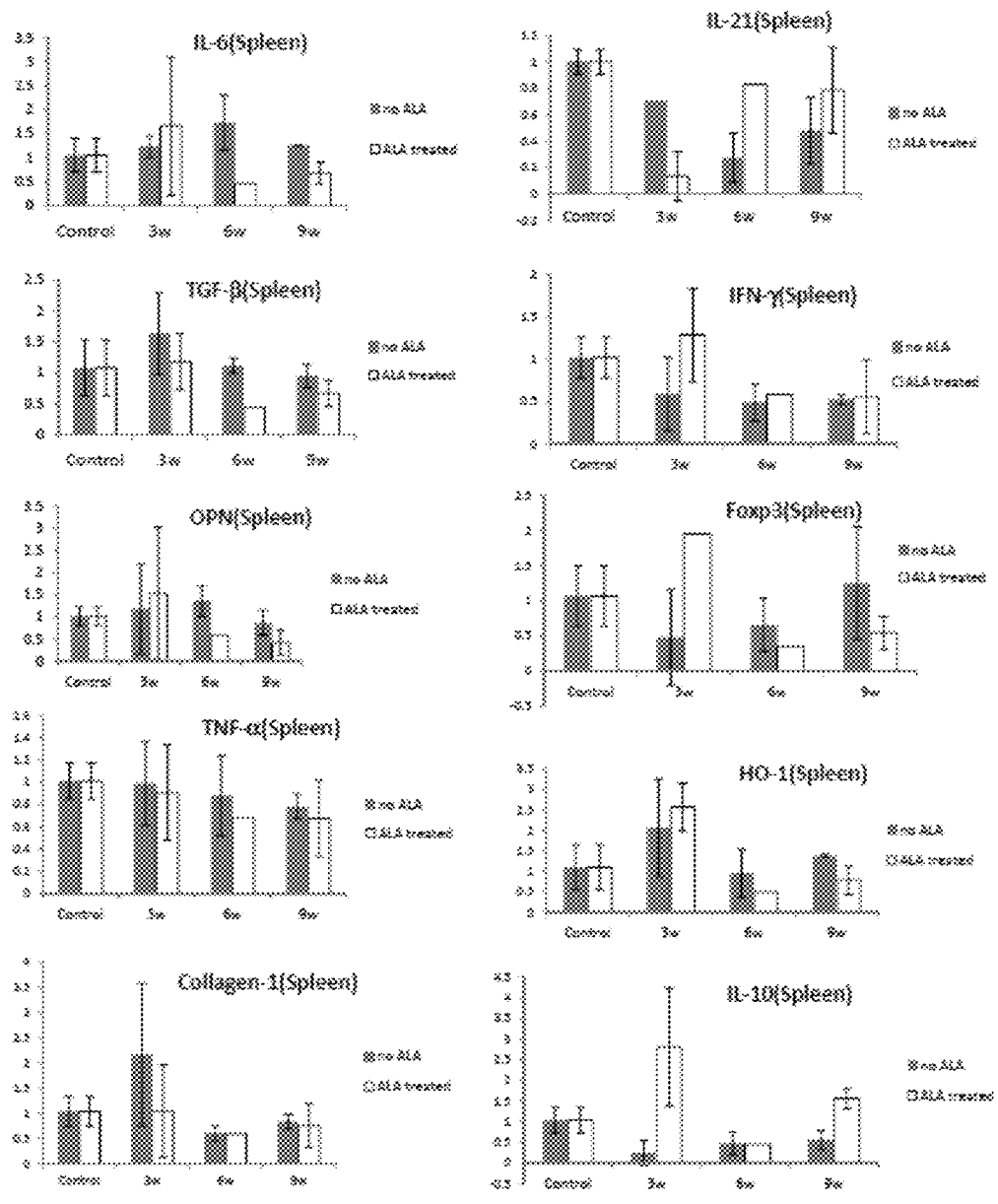
FIG. 24 is a set of diagrams showing the results of the expression of marker genes in the spleen of a pathological mouse model of scleroderma with ALA administration.

The results of the spleen are shown in FIG. 24.

In the spleen, a tendency of increase in FoxP3, a regulatory T cell marker (right, third from the top in FIG. 24), and in IL-10 (bottom right in FIG. 24), an inflammation inhibitory cytokine produced by regulatory T cells, by ALA administration was observed, suggesting the activation of regulatory T cells by ALA.

[Kidney]

Figure 25:
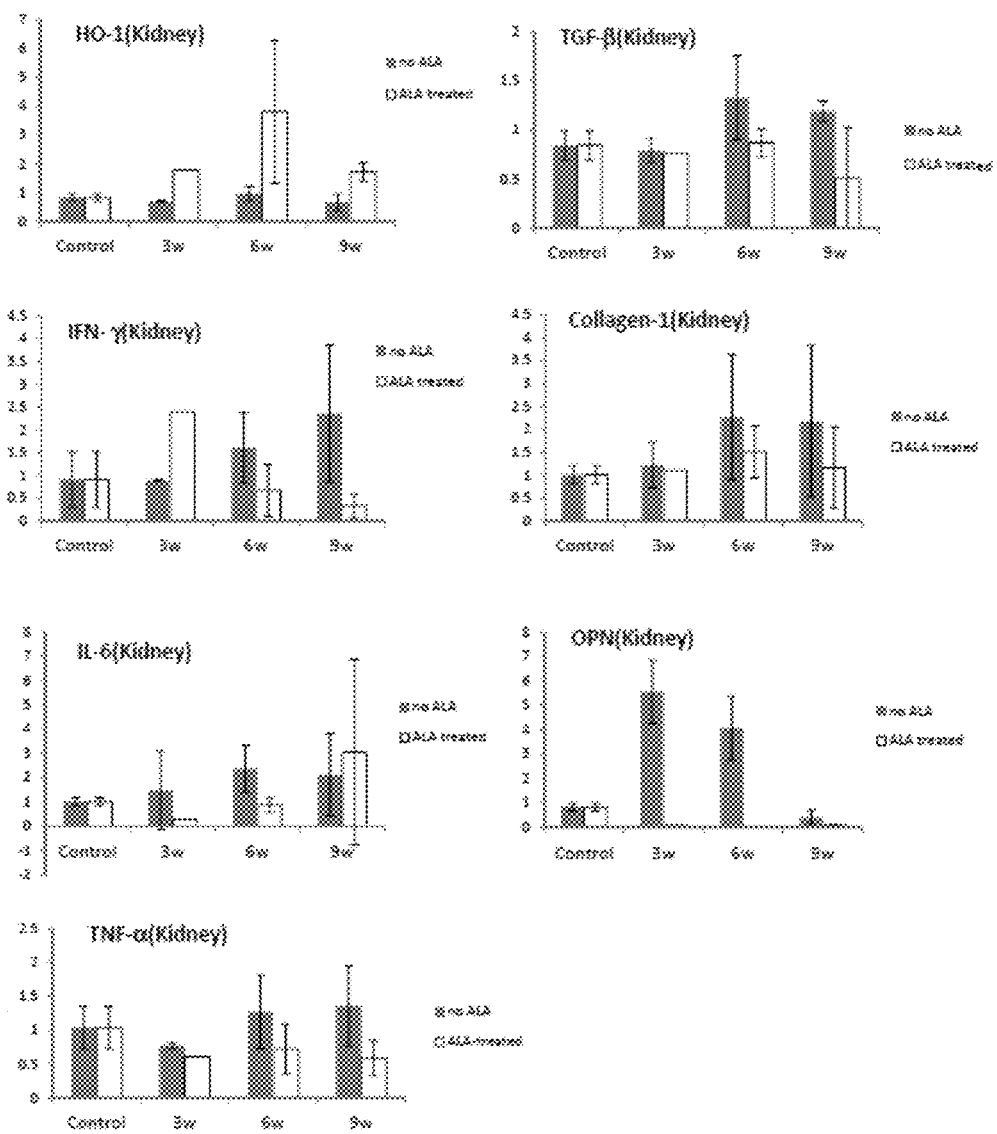
FIG. 25 is a set of diagrams showing the results of the expression of marker genes in the kidney of a pathological mouse model of scleroderma with ALA administration.

The results of the kidney are shown in FIG. 25. In the kidney, immune tolerance is assumed to be induced, and an increase in HO-1 (top left in FIG. 25), which is induced by heme, and a tendency of decrease in the fibrosis marker Collagen-1 (right, second from the top in FIG. 25) and in the inflammation cytokine IL-6, and a decrease in osteopontin (OPN) (third from the top in FIG. 25) were observed, suggesting that ALA suppressed inflammation and prevented fibrosis.

INDUSTRIAL APPLICABILITY

The regulatory dendritic cell inducing agent as well as the immune tolerance inducing agent such as the preventive and/or therapeutic agent for allergic disease, and the preventive and/or therapeutic agent for autoimmune disease according to the present invention can be advantageously used in the pharmaceutical and medical fields.

The invention claimed is:

1. A method of inducing immune tolerance without light irradiation, comprising administering to a subject having an allergic disease or an autoimmune disease an immune tolerance inducing agent containing a compound represented by the following formula (I) or a salt thereof:

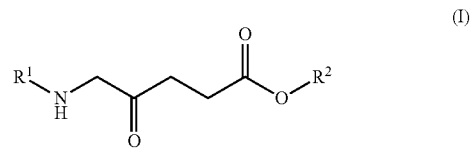

(I)

wherein $R^1$ represents a hydrogen atom or an acyl group; and $R^2$ represents a hydrogen atom, a linear or branched alkyl group, a cycloalkyl group, an aryl group, or an aralkyl group; and wherein administration of the immune tolerance inducing agent is oral, inhalation, or intravenous.

2. The method of inducing immune tolerance according to claim 1, wherein $R^1$ and $R^2$ each represents a hydrogen atom.

3. The method of inducing immune tolerance according to claim 1, wherein the immune tolerance inducing agent further contains an iron compound.

4. The method of inducing immune tolerance according to claim 3, wherein the iron compound is one or more compound(s) selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylene diaminetetraacetate, iron ammonium ethylene diaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

5. The method of inducing immune tolerance according to claim 3, wherein the iron compound is sodium ferrous citrate.

6. The method of inducing immune tolerance according to claim 1, comprising administering the immune tolerance inducing agent to a subject in need of inducing a regulatory dendritic cell.

7. The method for inducing immune tolerance according to claim 1, wherein the allergic disease is atopic dermatitis.

8. The method for inducing immune tolerance according to claim 1, wherein the autoimmune disease is scleroderma.

9. The method for inducing immune tolerance according to claim 2, wherein the immune tolerance inducing agent further contains an iron compound.

10. The method for inducing immune tolerance according to claim 9, wherein the iron compound is one or more compound(s) selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylene diaminetetraacetate, iron ammonium ethylene diaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

11. The method for inducing immune tolerance according to claim 9, wherein the iron compound is sodium ferrous citrate.

12. The method for inducing immune tolerance according to claim 2, comprising administering the immune tolerance inducing agent to a subject in need of inducing a regulatory dendritic cell.

13. The method for inducing immune tolerance according to claim 3, comprising administering the immune tolerance inducing agent to a subject in need of inducing a regulatory dendritic cell.

14. The method for inducing immune tolerance according to claim 4, comprising administering the immune tolerance inducing agent to a subject in need of inducing a regulatory dendritic cell.

15. The method for inducing immune tolerance according to claim 5, comprising administering the immune tolerance inducing agent to a subject in need of inducing a regulatory dendritic cell.

16. The method for inducing immune tolerance according to claim 9, comprising administering the immune tolerance inducing agent to a subject in need of inducing a regulatory dendritic cell.

17. The method for inducing immune tolerance according to claim 10, comprising administering the immune tolerance inducing agent to a subject in need of inducing a regulatory dendritic cell.

18. A method for inducing immune tolerance without light irradiation, comprising administering to a subject having an allergic disease or an autoimmune disease a) a compound represented by the following formula (I) or a salt thereof:

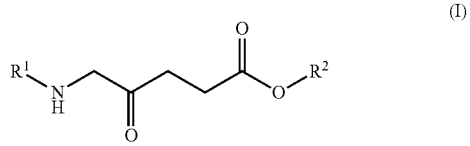

wherein $R^1$ represents a hydrogen atom or an acyl group; and $R^2$ represents a hydrogen atom, a linear or branched alkyl group, a cycloalkyl group, an aryl group, or an aralkyl group; and b) an iron compound; to the subject at the same time or in tandem; and wherein administration of compounds (a) and (b) is oral, inhalation, or intravenous.

19. The method of claim 1, wherein administration of the immune tolerance inducing agent is oral.

20. The method of claim 18, wherein administration of compounds (a) and (b) is oral.

\* \* \* \* \*